United States Patent
Tsai et al.

(10) Patent No.: US 11,952,469 B2
(45) Date of Patent: Apr. 9, 2024

(54) HYDROGEL COMPOSITION WITH THERMOS-SENSITIVE AND IONIC REVERSIBLE PROPERTIES, CARRIER, METHOD FOR PREPARING AND METHOD OF USE THEREOF

(71) Applicant: National Taiwan University of Science and Technology, Taipei (TW)

(72) Inventors: Hsieh-Chih Tsai, New Taipei (TW); Shuian-Yin Lin, Hsinchu County (TW); Hsiao-Ying Chou, New Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 147 days.

(21) Appl. No.: 17/219,915

(22) Filed: Apr. 1, 2021

(65) Prior Publication Data

US 2022/0135748 A1 May 5, 2022

(30) Foreign Application Priority Data

Nov. 5, 2020 (TW) .................................. 109138731

(51) Int. Cl.
*C08J 3/075* (2006.01)
*A61L 26/00* (2006.01)
*C08J 3/24* (2006.01)

(52) U.S. Cl.
CPC ........... *C08J 3/075* (2013.01); *A61L 26/0052* (2013.01); *A61L 26/008* (2013.01); *C08J 3/24* (2013.01); *C08J 2305/04* (2013.01); *C08J 2333/26* (2013.01); *C08J 2371/02* (2013.01)

(58) Field of Classification Search
CPC ....... C08J 3/075; C08J 2305/04; A61L 26/008
See application file for complete search history.

(56) References Cited

U.S. PATENT DOCUMENTS

| 2011/0165244 A1* | 7/2011 | Neff | A61K 47/56 424/78.17 |
| 2013/0115196 A1* | 5/2013 | Hantash | A61K 47/42 435/377 |

FOREIGN PATENT DOCUMENTS

CN 106474051 A 3/2017

OTHER PUBLICATIONS

Chou, H-Y. et al. "Design of an Interpenetrating Polymeric Network Hydrogel Made of Calcium-Alginate from a Thermos-Sensitive Pluronic Template as a Thermal-Ionic Reversible Wound Dressing" Polymers 2020, 12, 2138, 1-15 (Year: 2020).*
Nie, J. et al. "Construction of ordered structure in polysaccharide hydrogel: A review" Carbohydrate Polymers 205 (2019) 225-235 (Year: 2019).*
Grassi, G. et al. "Rheological properties of aqueous Pluronic-alginate systems containing liposomes" Journal of Colloid and Interface Science 301 (2006) 282-290. (Year: 2006).*
Hsiao-Ying Chou et al., "Design of an Interpenetrating Polymeric Network Hydrogel Made of Calcium-Alginate from a Thermos-Sensitive Pluronic Template as a Thermal-Ionic Reversible Wound Dressing", Polymers, Sep. 18, 2020, 12, 2138.

* cited by examiner

*Primary Examiner* — Andrew S Rosenthal
(74) *Attorney, Agent, or Firm* — CKC & Partners Co., LLC

(57) ABSTRACT

The present disclosure provides a method for preparing a hydrogel composition with thermos-sensitive and ionic reversible properties and the hydrogel composition prepared by the method. Related application products of the hydrogel composition of the present disclosure include wound dressings, drug carriers, three-dimensional cellular scaffolds, soluble microspheres, and cell capture and release systems, wherein the hydrogel composition with thermos-sensitive and ionic reversible properties has good in vitro and in vivo stability and high biocompatibility, and is non-toxic. The hydrogel composition can be removed and replaced by washing with metal chelating aqueous solution at low temperature.

19 Claims, 16 Drawing Sheets

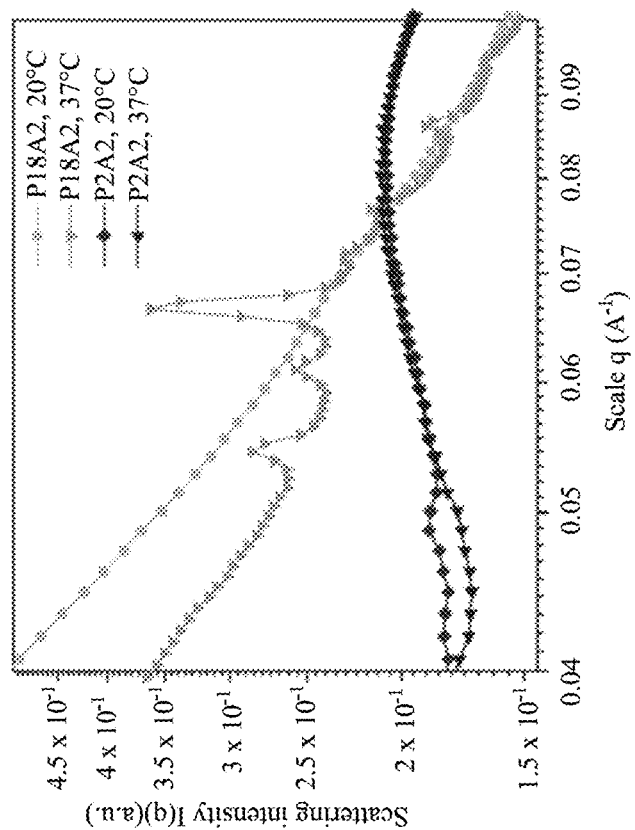
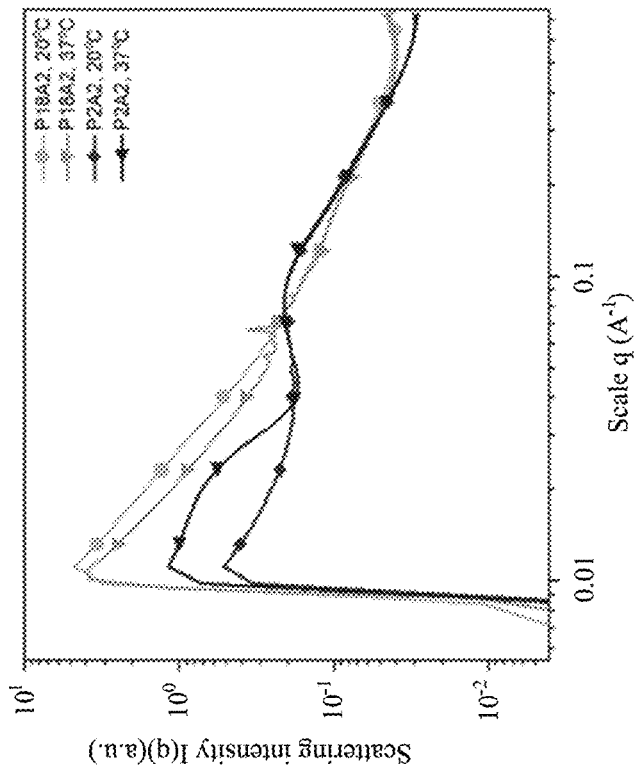
Fig. 12B
Fig. 12A

HYDROGEL COMPOSITION WITH THERMOS-SENSITIVE AND IONIC REVERSIBLE PROPERTIES, CARRIER, METHOD FOR PREPARING AND METHOD OF USE THEREOF

CROSS-REFERENCE TO RELATED APPLICATION

This application claims priority to Taiwan Application Ser. No. 109138731, filed on Nov. 5, 2020, which is herein incorporated by reference in its entirety.

BACKGROUND

Field of Invention

The present invention relates to a method for preparing a hydrogel composition with thermos-sensitive and ionic reversible properties and the hydrogel composition prepared by the method.

Description of Related Art

The study of skin wound healing is an important part of the recent development of tissue engineering. The main purpose of traditional wound dressings (such as gauze) is to provide a barrier to keep the wound dry and evaporate wound exudates, while preventing pathogens from entering the wound. However, since the wound dressing absorbs the exudate and dries, it is tightly attached to the wound. When changing the wound dressing, the wound dressing must be removed by tearing off, such that the secondary injury to the wound cannot be avoided.

In the prior art, which disclosed a preparation method for polymer composite hydrogel dressing compositions. The compositions are prepared by physical or chemical mix, calcium ions are crosslinked first and then the physical interaction is performed. The preparation method will obtain a heterogeneity distribution network in the compositions, and the reversible property of the compositions does not discuss.

Currently, there has cell culture scaffolds made of microsphere-type hydrogel composite materials. Unlike ordinary cell culture dishes, cells will grow into a three-dimensional structure or grow on the surface of hydrogel in a two-dimensional, and cell culture scaffolds are expected to be applied to stem cells culture and transplantation. After the cells have grown to a certain amount, the hydrogel needs to be removed before the cells are implanted into the body. However, if the hydrogel cannot be completely removed, it will affect clinical applications.

Therefore, based on the above defects, the prior art needs to be improved. On the other hand, ice salt water is not used to remove the wound dressing, and three-dimensional cell culture microspheres are used for a large-scale cell culture. At present, all microspheres are designed to be insoluble. Therefore, how to separate the microspheres and the cultured cells is very important after the cells detach from the microspheres.

SUMMARY

In order to solve the above problems, a skilled person in the art urgently need to develop novel method for preparing hydrogel composition with thermos-sensitive and ionic reversible properties, and the hydrogel composition with thermos-sensitive and ionic reversible properties, wherein the application of the hydrogel composition with thermos-sensitive and ionic reversible properties includes wound dressings, medical compositions, drug carriers, cell three-dimensional scaffolds, soluble microspheres and cell replenishment systems.

The present disclosure provides a method for preparing a hydrogel composition with thermos-sensitive and ionic reversible properties, comprising following steps: providing a thermos-sensitive polymer; providing an ionic polymer; dissolving and mixing the thermos-sensitive polymer and the ionic polymer in a solvent to obtain an initial solution; and performing a mixing process with the initial solution and an ionic crosslinking agent, wherein when the initial solution and the ionic crosslinking agent are contact, crosslinking occur to obtain the hydrogel composition with thermos-sensitive and ionic reversible properties, wherein the hydrogel composition with thermos-sensitive and ionic reversible properties has ordered structure.

In some embodiments, the thermos-sensitive polymer comprises amphiphilic triblock copolymer or N-isopropylacrylamide (NIPAAm), and the ionic polymer comprises polysaccharide having at least one carboxylic acid.

In some embodiments, the amphiphilic triblock copolymer comprises poloxamer, the poloxamer is sequentially composed with poly-ethylene oxide (PEO)—poly-propylene oxide (PPO)—PEO, wherein the polysaccharide having the at least one carboxylic acid comprises mannuronic acid and guluronic acid.

In some embodiments, the polysaccharide is alginate.

In some embodiments, the step of dissolving and mixing the thermos-sensitive polymer and the ionic polymer in a solvent comprises a weight ratio of the thermos-sensitive polymer and the ionic polymer is from 1:0.001 to 1:0.6.

In some embodiments, the ionic crosslinking agent comprises one or more solutions of monovalent to tetravalent metal cations, a metal chelating agent, or a combination thereof.

In some embodiments, the one or more solutions of monovalent to tetravalent metal cations are $Li^+$, $Na^+$, $K^+$, $Cu^+$, $Ag^+$, $Au^+$, $Cu^{+2}$, $Be^{+2}$, $Mg^{+2}$, $Ca^{+2}$, $Sr^{+2}$, $Ba^{+2}$, $Zn^{+2}$, $Sn^{+2}$, $Fe^{+2}$, $Pb^{+2}$, $Co^{+2}$, $Ni^{+2}$, $Mn^{+2}$, $Cd^{+2}$, $Au^{+3}$, $Al^{+3}$, $Ga^{+3}$, $In^{+3}$, $Fe^{+3}$, $Co^{+3}$, $Ni^{+3}$, $Ce^{+3}$, $Se^{+3}$, $Ce^{+4}$, $Se^{+4}$, $Ti^{+4}$, or a combination thereof.

In some embodiments, the step of dissolving and mixing the thermos-sensitive polymer and the ionic polymer in a solvent comprises obtaining the initial solution at a low temperature.

In some embodiments, the low temperature is from 0° C. to 20° C.

In some embodiments, the step of performing the mixing process with the initial solution and the ionic crosslinking agent comprises mixing the initial solution and the ionic crosslinking agent at a predetermined temperature, wherein when the predetermined temperature is from 10° C. to 45° C., the hydrogel composition with thermos-sensitive and ionic reversible properties is in a gel state.

In some embodiments, the mixing process comprises dialysis, microfluidics, titration, electrospinning, emulsion polymerization, reprecipitation, or a combination thereof.

In some embodiments, the ordered structure comprises a face-centered cubic crystal structure, a body-centered cubic crystal structure, a hexagonal close-packed crystal structure, a layered structure, or a combination thereof.

The present disclosure also provides a hydrogel composition with thermos-sensitive and ionic reversible properties, comprising a thermos-sensitive polymer and an ionic polymer. Wherein the hydrogel composition is analyzed by Raman spectroscopy when the hydrogel composition is in a gel state, the hydrogel composition comprises Raman shift peaks from about 1460 cm$^{-1}$ to about 1490 cm$^{-1}$ and from about 1730 cm$^{-1}$ to about 1770 cm$^{-1}$, and a Raman mapping image of the hydrogel composition presents an ordered structure. Wherein the hydrogel composition is analyzed by small-angle X-ray scattering (SAXS) when the hydrogel composition is in the gel state, the hydrogel composition comprises a scattering intensity peak in an interval from 0.05 A$^{-1}$ to 0.08 A$^{-1}$.

In some embodiments, the thermos-sensitive polymer comprises amphiphilic triblock copolymer or N-isopropylacrylamide (NIPAAm), and the ionic polymer comprises polysaccharide having at least one carboxylic acid.

In some embodiments, the amphiphilic triblock copolymer comprises poloxamer, the poloxamer is sequentially composed with poly-ethylene oxide (PEO)—poly-propylene oxide (PPO)—PEO, wherein the polysaccharide having the at least one carboxylic acid comprises mannuronic acid and guluronic acid.

In some embodiments, the polysaccharide is alginate.

In some embodiments, the ordered structure is a layered structure, the layered structure is composed of a plurality of layers, an interval between two adjacent layers of the plurality of layers is from about 40 μm to about 600 μm.

The present disclosure also provides a carrier comprising the hydrogel composition with thermos-sensitive and ionic reversible properties according to above mentioned, wherein a form of the carrier comprises a wound dressing, a medical composition, a drug carrier, a cell three-dimensional scaffold or a soluble microsphere.

The present disclosure also provides a method of use of the hydrogel composition with thermos-sensitive and ionic reversible properties according to above mentioned, wherein when the hydrogel composition contacts a water solution having a temperature lowers than a lower critical solution temperature (LCST) of the hydrogel composition, a metal chelate aqueous solution, or a metal chelate aqueous solution having a temperature lower than the LCST of the hydrogel composition, the hydrogel composition transfers from a gel state to a solution state.

In some embodiments, the LCST is from 10° C. to 45° C.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion. The invention can be more fully understood by reading the following detailed description of the embodiment, with reference made to the accompanying drawings as follows.

FIG. 4A is 1.5 g Pluronic® F127 (Plu)-150 mg alginate (Alg), FIG. 4B is 1.5 g Plu-100 mg Alg, FIG. 4C is 1.5 g Plu-50 mg Alg, and FIG. 4D is 1.5 g Plu-25 mg Alg.

FIG. 8A is 150 mg alginate, FIG. 8B is 100 mg alginate, FIG. 8C is 50 mg alginate, and FIG. 8D is 25 mg alginate.

FIG. 9A shows 150 mg of alginate crosslinked with calcium (scale bar is 200 μm), FIG. 9B shows 15% (w/v) PF127 (scale bar is 100 μm), FIG. 9C shows 15% (w/v) PF127 mixed with 25 mg calcium alginate (scale bar 100 μm), FIG. 9D shows 15% (w/v) PF127 mixed with 50 mg calcium alginate (scale bar 100 μm), FIG. 9E shows 15% (w/v) PF127 mixed with 100 mg of calcium alginate (scale bar 100 μm), and FIG. 9F shows 15% (w/v) PF127 mixed with 150 mg of calcium alginate (scale bar 100 μm).

FIGS. 10A to 10B are bar graphs showing the cytotoxicity test of the hydrogel compositions with thermos-sensitive and ionic reversible properties according to one embodiment of the present disclosure, in which FIG. 10A shows the cell survival rate of human skin keratinocytes (HaCaT) treated with the composition in the solution state (before gelation, without calcium ions), and FIG. 10B shows the cell survival rate of human skin keratinocytes (HaCaT) treated with the composition in the gel state (after gelation, with calcium ions).

FIG. 11A shows the result of Plu/Alg with mixing ratio 2:2 (P2A2) from Group A to Group D. FIG. 11B shows the results of the Plu/Alg mixing ratio of 20:2 (P20A2) from Group E to Group H. Please refer to the following embodiment for the detailed conditions of Groups A to H.

FIGS. 12A to 12D show a small-angle X-ray scattering (SAXS) patterns of one embodiment of the present disclosure. FIG. 12A shows the hydrogel compositions with the Plu/Alg mixing ratio of 2:2 and 18:2 gelling at 20° C. and 37° C.; FIG. 12B is a partial enlarged view of FIG. 12A; FIG. 12C shows the Plu 18 wt % alone gelling at 20° C. and 37° C.; FIG. 12D shows the changes in the scattering intensity of Plu 2 wt % (P2) and Plu 20 wt % (P20) gelling at 20° C. and 37° C.

DETAILED DESCRIPTION

Figure 1:
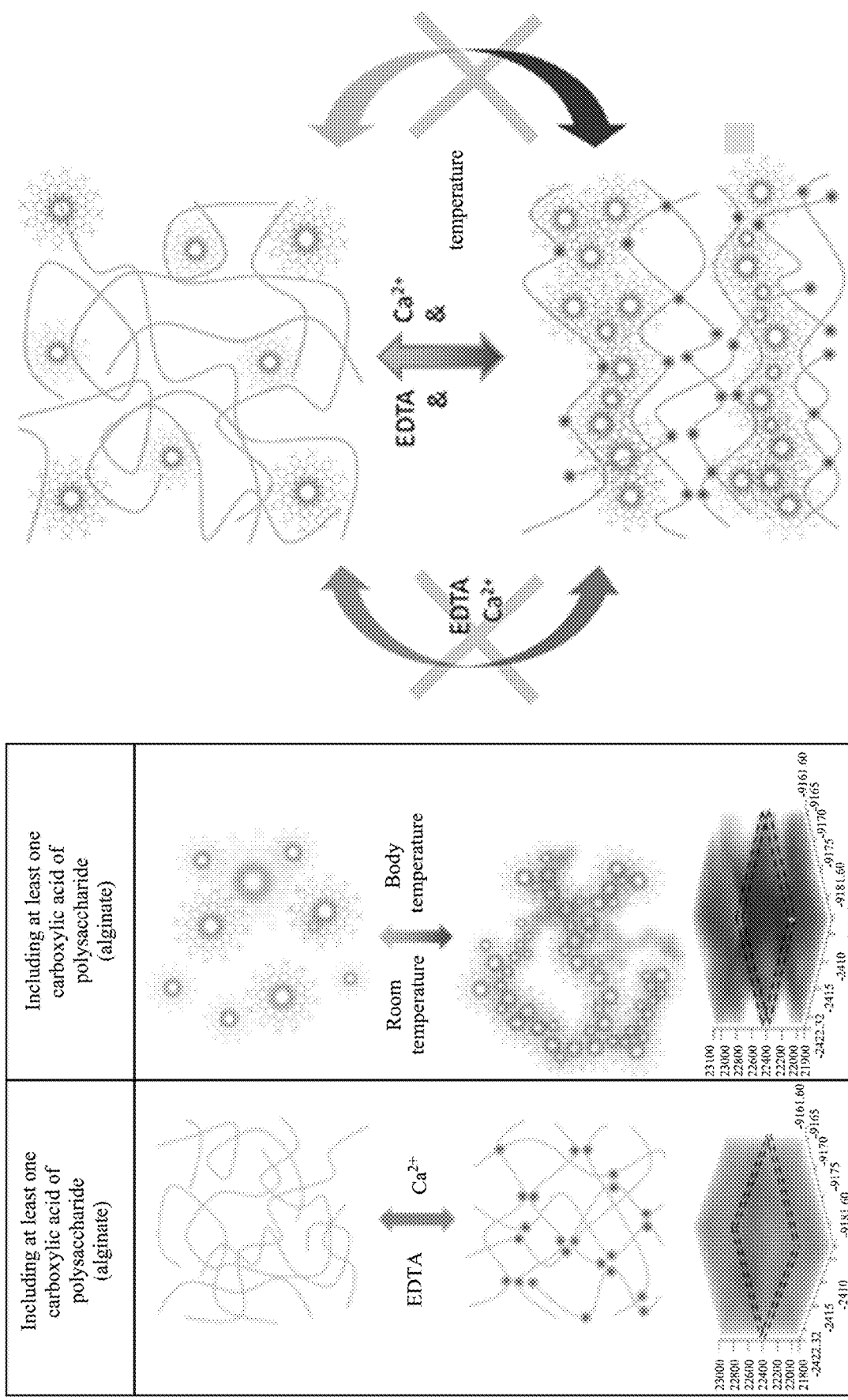
FIG. 1 is a schematic view of preparing a hydrogel composition with thermos-sensitive and ionic reversible properties according to one embodiment of the present disclosure.

The following disclosure provides detailed description of many different embodiments, or examples, for implementing different features of the provided subject matter. These are, of course, merely examples and are not intended to limit the invention but to illustrate it. In addition, various embodiments disclosed below may combine or substitute one embodiment with another, and may have additional embodiments in addition to those described below in a beneficial way without further description or explanation. In the following description, many specific details are set forth to provide a more thorough understanding of the present disclosure. It will be apparent, however, to those skilled in the art, that the present disclosure may be practiced without these specific details.

Further, spatially relative terms, such as "beneath," "over" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

In some embodiments, after gelation, the hydrogel composition with thermos-sensitive and ionic reversible properties is reversible. The amphiphilic triblock copolymer and polysaccharide polymer in the hydrogel composition interact with van der Waals force, hydrophilic and hydrophobic force, hydrogen bond, and interaction to form a gel by self-assembling. The amphiphilic triblock copolymer used in the present disclosure has a lower critical solution temperature (LCST), and the polysaccharide polymer is crosslinked by metal cations in the system. Thus, the present disclosure can reverse the hydrogel composition from the gel state to the solution state by controlling the metal ion content and temperature in the environment.

In some embodiments, the hydrogel composition with thermos-sensitive and ionic reversible properties can be used as a wound dressing including at least one lining, in which the lining can be a release film. In some examples, the wound dressing is in a sheet form, including two lining respectively located on opposite sides of the composition.

In some embodiments, the hydrogel composition with thermos-sensitive and ionic reversible properties includes the amphiphilic triblock copolymer and the polysaccharide polymer having at least one carboxylic acid.

In some embodiments, a concentration the amphiphilic triblock copolymer is from 10% (w/v) to 50% (w/v), such as 15%, 20%, 25%, 30%, 35%, 40%, 45%, or any value between any two of these values. A concentration of the polysaccharide polymer having at least one carboxylic acid is from 0.1% (w/v) to 10% (w/v), such as 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 6.0%, 7.0%, 8.0%, 9.0%, or any value between any two of these values.

In some embodiments, the amphiphilic triblock copolymer includes poloxamer, or the commercial name Pluronic®.

In some embodiments, poloxamers are nonionic triblock copolymers composed of a central hydrophobic chain of polyoxypropylene (poly-propylene oxide) flanked by two hydrophilic chains of polyoxyethylene (poly-ethylene oxide), which can be used to evaluate many drug delivery applications and demonstrate sensitivity to drug-resistant cancers in chemotherapy. Because the lengths of the polymer blocks can be customized, many different poloxamers have slightly different properties. For the generic term poloxamer, these copolymers are commonly named with the letter P (for poloxamer) followed by three digits: the first two digits multiplied by 100 give the approximate molecular mass of the polyoxypropylene core, and the last digit multiplied by 10 gives the percentage polyoxyethylene content (e.g. P407=poloxamer with a polyoxypropylene molecular mass of 4000 g/mol and a 70% polyoxyethylene content).

In some embodiments, poloxamer can be poloxamer 407 which commercial name is Pluronic® F-127.

In some embodiments, the alginate can be sodium alginate.

In some embodiments, a weight ratio of Pluronic® F127 and sodium alginate is 1.25~2.75:0.025~0.15. In some examples, the weight ratio of Pluronic® F-127 and sodium alginate is 1.25:0.025~0.15, 1:0.02~0.12, 1.5: 0.025~0.15, 1:0.0167~0.1, 2.75:0.025~0.15, or 1:0.009~0.545. In some examples, the weight ration of Pluronic® F-127 and sodium alginate is 1:0.009, 1:0.01, 1:0.017, 1:0.018, 1:0.02, 1:0.022, 1:0.024, 1:0.026, 1:0.028, 1:0.03, 1:0.033, 1:0.035, 1:0.04, 1:0.045, 1:0.05, 1:0.055, 1:0.06, 1:0.065, 1:0.067, 1:0.07, 1:0.075, 1:0.08, 1:0.085, 1:0.09, 1:0.095, 1:0.1, 1:0.15, 1:0.2, 1:0.25, 1:0.3, 1:0.35, 1:0.4, 1:0.45, 1:0.5, or 1:0.545.

In some embodiments, the hydrogel composition with thermos-sensitive and ionic reversible properties can be used as a pharmaceutical composition, the pharmaceutical composition includes an active ingredient and a pharmaceutically acceptable excipients.

In some embodiments, the pharmaceutically acceptable excipients include, but are not limited to, disintegrants, binders, fillers, lubricants, suspending agent, solubilizer, and glidants.

In some embodiments, the disintegrants include, but are not limited to, agar-agar, alginic acid, calcium carbonate, carboxymethylcellulose, cellulose, clays, colloidal silica, croscarmellose sodium, crosslinked povidone, gum, silicon magnesium aluminometasilicate, methyl cellulose, polacrilin potassium, sodium alginate, low substituted hydroxypropyl cellulose, and crosslinked polyvinylpyrrolidone hydroxypropylcellulose, sodium starch glycolate, and starch.

In some embodiments, the binders include, but are not limited to, microcrystalline cellulose, hydroxymethyl cellulose, hydroxypropyl cellulose and polyvinyl pyrrolidone.

In some embodiments, the fillers include, but are not limited to, calcium carbonate, calcium phosphate, dibasic calcium phosphate, tribasic calcium sulfate, calcium carboxymethylcellulose, cellulose, dextrin, salt, dextrin, dextrose, fructose, lactitol, lactose, carbonate, magnesium oxide, maltitol, maltodextrin, maltose, sorbitol, starch, sucrose, sugar, and xylitol.

In some embodiments, the lubricants include, but are not limited to, agar, calcium stearate, ethyl oleate, ethyl laureate, glycerin, glyceryl palmitostearate, hydrogenated vegetable oil, magnesium oxide, magnesium stearate, mannitol, poloxamer, ethylene glycol, sodium benzoate, sodium lauryl sulfate, sodium stearyl acid, sorbitol, stearic acid, talc and zinc stearate.

In some embodiments, the suspending agents include, but are not limited to mannitol, carboxymethyl cellulose (CMC), and sodium carboxymethyl cellulose (CMC-Na).

In some embodiments, the solubilizers include, but are not limited to hydroxypropyl-beta-cyclodextrin, tween 80, and castor oil.

In some embodiments, the glidants includes, but are not limited tomagnesium stearate, silicon dioxide, magnesium trisilicate, powdered cellulose, starch, talc, tribasic calcium phosphate, calcium silicate, magnesium silicate, colloidal silica, and silicon hydrogel.

In some embodiments, the active ingredient includes growth factor. The growth factor includes, but is not limited toepidermal growth factor (EGF), ephrins, erythropoietin (EPO), fibroblast growth factor (FGF), insulin-like growth factors (IGF), interleukins, neurotrophins, and vascular endothelial growth factor (VEGF).

In some embodiments, the Pluronic® F-127 and different amounts of sodium alginate are dissolved in water, after mixing, an initial solution was obtained. After the sodium alginate and the Pluronic® F-127 in the initial solution were crosslinked, a side of a dialysis membrane containing the initial solution was obtained the hydrogel composition with thermos-sensitive and ionic reversible properties. In some other embodiments, microfluid, titration, electrospinning, or reprecipitation treatment can also be used to replace the dialysis treatment. In some examples, when the hydrogel composition was prepared by the titration, the preparation temperature of the initial solution was from 0° C. to 10° C., such as 1° C., 2° C., 3° C., 4° C., 5° C., 6° C., 7° C., 8° C., 9° C., or any value between any two of these values.

In some embodiments, the hydrogel composition with thermos-sensitive and ionic reversible properties of the present disclosure in the gel state can be formed in an ordered structure. As used herein, "ordered structure" is intended to when the hydrogel composition is in gel state, the hydrogel composition is orderly formed in a face-centered cubic crystal structure, body-centered cubic crystal structure, hexagonal close-packed crystal structure, layered structure, or a combination thereof.

In some embodiments, the ionic crosslinking agent includes, but is not limited to one or more solutions of monovalent to tetravalent metal cations, a metal chelating agent, or a combination thereof. In some examples, ionic crosslinking agent includes the solution of monovalent metal cations or the metal chelating agent.

In some embodiments, the monovalent to tetravalent metal cations in the ionic crosslinking agent are $Li^+$, $Na^+$, $K^+$, $Cu^+$, $Ag^+$, $Au^+$, $Cu^{+2}$, $Be^{+2}$, $Mg^{+2}$, $Ca^{+2}$, $Sr^{+2}$, $Ba^{+2}$, $Zn^{+2}$, $Sn^{+2}$, $Fe^{+2}$, $Pb^{+2}$, $Co^{+2}$, $Ni^{+2}$, $Mn^{+2}$, $Cd^{+2}$, $Au^{+3}$, $Al^{+3}$, $Ga^{+3}$, $In^{+3}$, $Fe^{+3}$, $Co^{+3}$, $Ni^{+3}$, $Ce^{+3}$, $Se^{+3}$, $Ce^{+4}$, $Se^{+4}$, $Ti^{+4}$, or a combination thereof.

In some embodiments, the metal chelating agent is one or more monovalent to tetravalent metal cations of ethylenediaminetetraacetic acid (EDTA), such as Ca-EDTA.

Although a series of operations or steps are used below to describe the method disclosed herein, an order of these operations or steps should not be construed as a limitation to the present invention. For example, some operations or steps may be performed in a different order and/or other steps may be performed at the same time. In addition, all shown operations, steps and/or features are not required to be executed to implement an embodiment of the present invention. In addition, each operation or step described herein may include a plurality of sub-steps or actions.

Preparation 1 Preparation of the Hydrogel Composition with Thermos-Sensitive and Ionic Reversible Properties 1.5 g of Pluronic® F-127 (hereinafter Plu) and different weights such as 0.15 g, 0.1 g, 0.05 g or 0.025 g of sodium alginate (hereinafter Alg, purchased from Sigma-Aldrich®, 250 g, extracted from brown algae) were respectively dissolved in 10 mL of water and stirred with magnet stir bar for 24 hours, the initial solution (hereinafter Plu-Alg solution) was obtained. Sodium alginate includes mannuronic acid blocks and guluronic acid blocks. In some examples, Plu and Alg were added into water and heated temporary to 37° C. until completely dissolved.

Next, an ionic crosslinking agent and a dialysis membrane were provided, wherein the ionic crosslinking agent included, but was not limited to one or more solutions of monovalent to tetravalent metal cations (such as calcium sulfate, $CaSO_4$), a metal chelating agent (such as Ca-EDTA), or a combination thereof. The initial solution and the ionic crosslinking agent were respectively placed into the opposite two sides of the dialysis membrane with a molecular weight cutoff of 1,000 Da to 50,000 Da, and dialysis was performed at a temperature of 10° C. to 45° C. The hydrogel composition crosslinked in the dialysis membrane was benefit to the shaping of the material (according to the type of dialysis membrane, it can be shaped into thin film or various types of hydrogel). Then, Plu and Alf in the initial solution were crosslinked, and the hydrogel composition with thermos-sensitive and ionic reversible properties at one of the sides of the dialysis membrane having the initial solution was obtained. In one example, the temperature for dialysis was from 10° C. to 45° C.

Dialysis can be performed in many ways. In some examples, the initial solution was placed in the dialysis membrane so that the initial solution was covered by the dialysis membrane; the dialysis membrane having the initial solution was placed into the ionic crosslinking agent containing 5 g/L calcium chloride ($CaCl_2$) at 4° C. for dialysis, and a hydrogel composition with thermos-sensitive and ionic reversible properties was obtained in the dialysis membrane. In some examples, a container with dialysis membrane was provided, and the container was divided into two impermeable areas by the dialysis membrane. These areas were defined upper and lower areas, front and rear areas, or left and right areas. The initial solution and the ionic crosslinking agent containing 5 g/L calcium chloride solution were respectively placed into different areas separated by the dialysis membrane, and dialysis was performed at a temperature of 10° C. to 45° C.

In some examples, during dialysis, the guluronic acid blocks (hereinafter G block) were ion exchanged with calcium chloride with divalent cations, so that one of the G blocks were crosslinked with the other one of the G blocks. Meanwhile, the dialysis method was also used to dialyze non-crosslinked molecules (such as sodium alginate) to the outside of the dialysis membrane. In some examples, the initial solution was placed in the dialysis membrane with the molecular weight cutoff of 1,000 to 50,000 Da, and then was placed in to 5 g/L calcium chloride solution at 4° C. for dialysis until dynamic equilibrium (for example, the number of crosslinked G blocks in the dialysis membrane and/or the number of non-crosslinked molecules in the dialysis membrane tended to be stable), the dialysis was completed. The ionic crosslinking agent was slowly passed through the dialysis membrane and was reacted with the initial solution, the hydrogel composition with thermos-sensitive and ionic reversible properties of the present disclosure was formed in an ordered structure in the gel state. The schematic view of preparing a hydrogel composition with thermos-sensitive and ionic reversible properties of the present disclosure is shown in FIG. 1.

Preparation 2. Preparation of the Hydrogel Composition with Thermos-Sensitive and Ionic Reversible Properties 1.5 g of Plu and different weights such as 0.15 g, 0.1 g, 0.05 g or 0.025 g of sodium Alg were respectively dissolved in 10 mL of water and stirred with magnet stir bar for 24 hours, the initial solution (hereinafter Plu-Alg solution) was obtained. Next, an ionic crosslinking agent was provided, wherein the ionic crosslinking agent included, but was not limited to one or more solutions of monovalent to tetravalent metal cations (such as calcium sulfate, $CaSO_4$), a metal chelating agent (such as Ca-EDTA), or a combination thereof. The initial solution and the ionic crosslinking agent were respectively placed into a dropper and a beaker, the temperature of the initial solution was from 0° C. to 10° C. Subsequently, the initial solution was titrated into the beaker at a rate of 0.01~2 mL/min. When the initial solution was in contact with the ionic crosslinking agent at 10° C. to 45° C., the hydrogel microspheres with thermos-sensitive and ionic reversible properties were obtained. In some examples, the particle size of the hydrogel microspheres was control by the speed of titration, the particle size was from about 0.5 mm to about 5 mm, such as 0.6 mm, 0.7 mm, 0.8 mm, 0.9 mm, 1.0 mm, 1.2 mm, 1.4 mm, 1.6 mm, 1.8 mm, 2.0 mm, 2.5 mm, 3.0 mm, 3.5 mm, 4.0 mm, 4.5 mm, or any value between any two of these values.

Preparation 3. Preparation of the Hydrogel Composition with Thermos-Sensitive and Ionic Reversible Properties by Microfluid 1.5 g of Plu and different weights such as 0.15 g, 0.1 g, 0.05 g or 0.025 g of Alg were respectively dissolved in 10 mL of water and stirred with magnet stir bar for 24 hours, the initial solution (Plu-Alg solution) was obtained. In some examples, Plu and Alg were added into water and heated temporary to 37° C. until completely dissolved.

Figure 2:
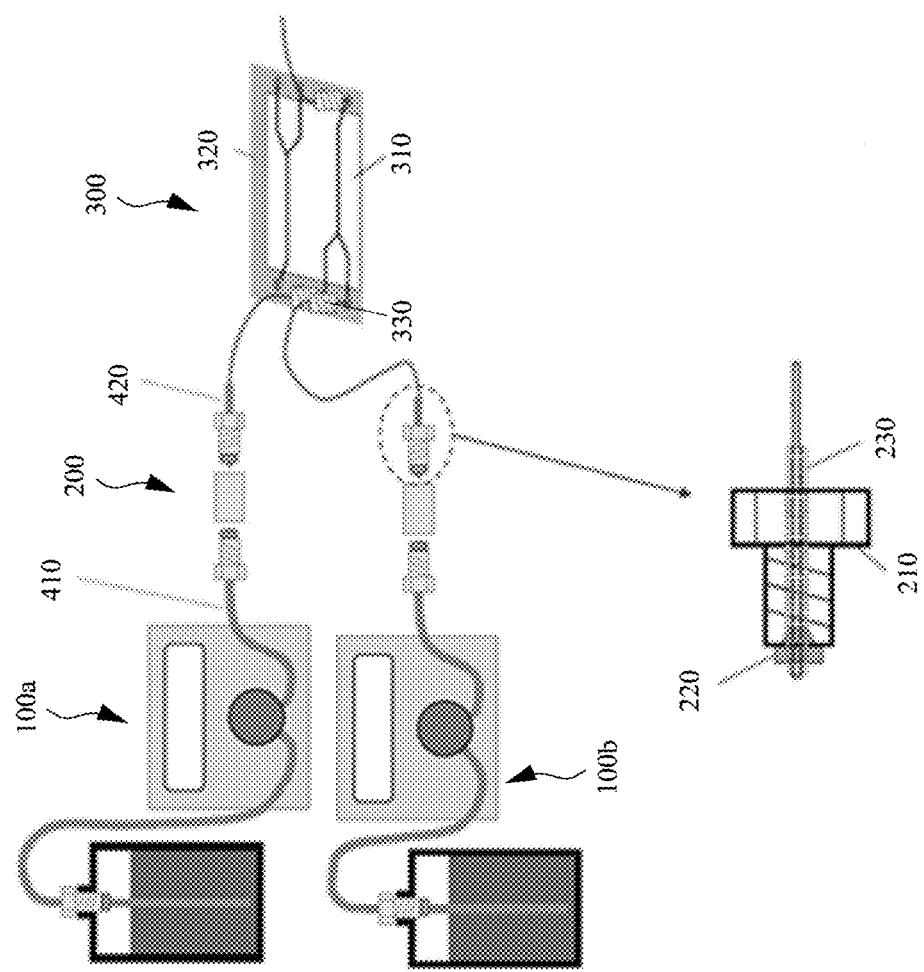
FIG. 2 is a schematic view of a microfluidic for a hydrogel microsphere according to one embodiment of the present disclosure.

Next, an ionic crosslinking agent was provided, wherein the ionic crosslinking agent included, but was not limited to one or more oil phase solutions of monovalent to tetravalent metal cations (such as calcium sulfate, $CaSO_4$), a metal chelating agent (such as Ca-EDTA), or a combination thereof. As shown in FIG. 2, the initial solution (Plu-Alg solution) and the ionic crosslinking agent were respectively filled into different pump 100a and pump 100b, and the temperature of the initial solution was from 0° C. to 10° C. Subsequently, the initial solution and the ionic crosslinking agent were respectively pumped into a microfluid 300 in a flow rate of 100 to 1000 microliters per minute (μL/min) and a flow rate of 800 μL/min to 8000 μL/min through connectors 200, and hydrogel microspheres were flowed and preserved in the deionized water. The Pump 100a and the pump 100b were respectively connected to the connectors 200 through two first tubes 410, and the connectors 200 were connected to the microfluid 300 by two second tubes 420, respectively. In some examples, each of the connectors 200 included nut 210, ferrule 220, and sleeve 230, wherein one end of the sleeve 230 having the ferrule 220 was connected to the first tube 410, and the other end of the sleeve 230 was connected to the second tubes 420. The nut 210 surrounded at central part of the sleeve 230. In one example, the dimensions of the nut 210, the ferrule 220, and the sleeve 230 were all 0.8 mm. In some examples, the microfluid 300 had a microfluidic chip 310 (iLiNP1.0), a chip holder 320 clamping the microfluidic chip 310, and a chip connector 330 connected with the second tubes 420 and the microfluidic chip 310. In some examples, the first tube 410 having 1/16 inch was conversed to 0.5 mm of the second tube 420 by the connector 200. In one example, the second tube 420 was capillary.

Example 1. Reversibility Test of Hydrogel Composition with Thermos-Sensitive and Ionic Reversible Properties The initial solution prepared from the Preparation 1 is divided into following three Groups A, B, and C.

Group A is reversibility test of hydrogel composition with thermos-sensitive property: 10 mL of the initial solution was placed into a 25 mL sample tube and heated to 37° C. for 4 hours to observe whether there is gel formation. If the gel is formed, the gel is then placed at 4° C. for 4 hours to observe whether the gel reverses to the solution state.

Group B is reversibility test of hydrogel composition with ionic reversible property: 2 mL of the initial solution was placed into the dialysis membrane with the molecular weight cutoff of 1,000 to 50,000 Da, and was dialyzed with 5 g/L calcium sulfate at 25° C. for 24 hours, and then was placed in to a sample tube to observe whether there is gel formation. If the gel is formed, the gel is then washed by 0.1 M of sodium chloride for 24 hours to observe whether the gel reverses to the solution state.

Group C is reversibility test of hydrogel composition with thermos-sensitive and ionic reversible properties: 2 mL of the initial solution was placed into the dialysis membrane with the molecular weight cutoff of 1,000 to 50,000 Da, and was dialyzed with 5 g/L calcium sulfate at 0° C. to 37° C. for 24 hours, and then was placed in to a sample tube to observe whether there is gel formation. If the gel is formed, the gel is then immersed in the phosphate buffered saline (PBS) at 4° C. for 24 hours to observe whether the gel reverses to the solution state.

Figure 3:
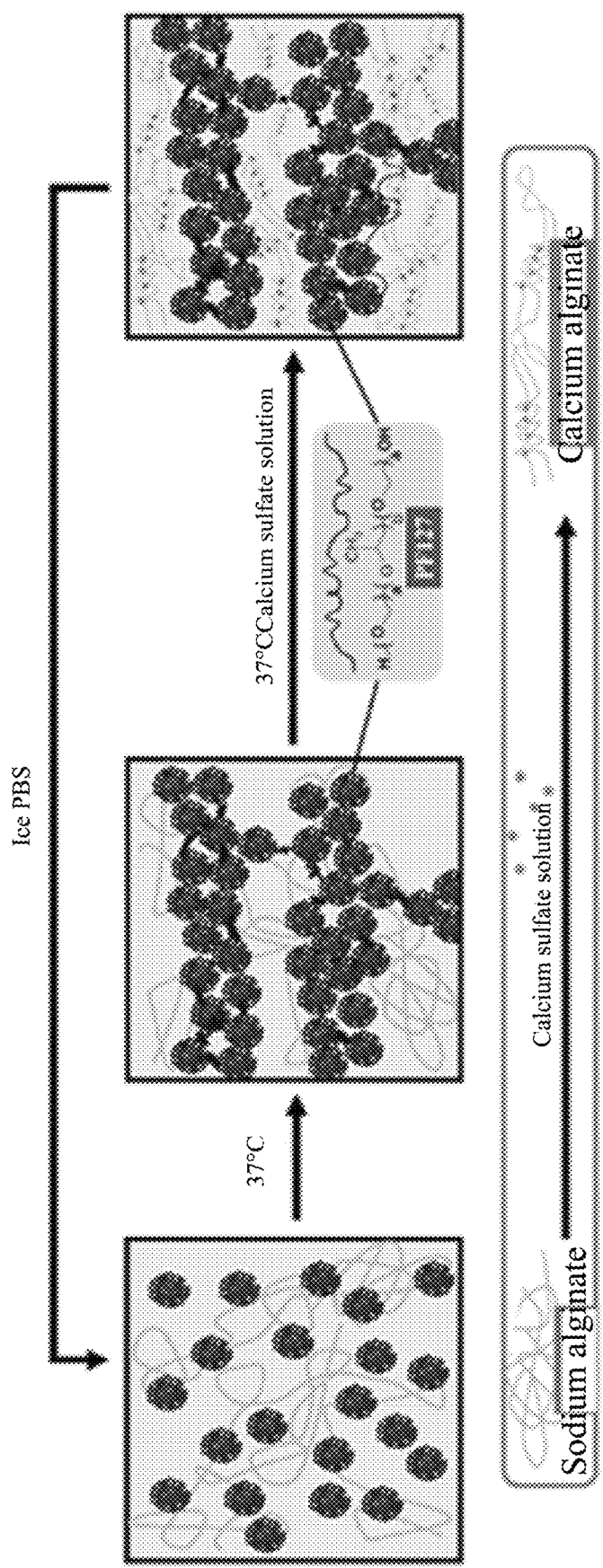
FIG. 3 is a schematic view of reversibility of the hydrogel composition with thermos-sensitive and ionic reversible properties according to one embodiment of the present disclosure.

The results of the above three groups suggest that the initial solution of Group A in the sample tube did not flow downwards at 37° C. while the sample tube was inversion, the gel was formed; next, the gel reversed to solution state after the temperature was cooled down to 4° C. The initial solution of Group B in the sample tube did not flow downwards after dialyzing with calcium sulfate for 24 hours while the sample tube was inversion, the gel was formed; next, the gel did not reverse to solution state after washing with sodium chloride. The initial solution of Group C in the sample tube did not flow downwards after dialyzing with calcium sulfate for 24 hours while the sample tube was inversion, the gel was formed; next, the gel reversed to solution state after washing with low temperature PBS. In one example, the low temperature PBS can be replaced with ice water or ice saline. The result of the present example suggests that the hydrogel composition with thermos-sensitive and ionic reversible properties of the present disclosure is different from the ordinary hydrogel, the hydrogel composition will not disintegration because of a single condition change (such as temperature), and it is easy to maintain the stability of the material structure during operation. The cross-linking of the hydrogel composition is controlled by the ions and temperature in the environment. The characteristic is that changing a single condition (such as temperature) cannot reverse the hydrogel from gel state to the liquid state. The schematic diagram of this example is shown in FIG. 3.

Example 2. Critical Change of the Hydrogel Composition with Thermos-Sensitive and Ionic Reversible Properties Between Solution State and Gel State The hydrogel compositions with thermos-sensitive and ionic reversible properties were prepared from four weight ratios of Plu-Alg solutions in the Preparation 1. A particle size analyzer (also known as dynamic light scattering (DLS)) was used to observe the changes of the four hydrogel compositions from the solution state to the gel state when the temperature rose from 20° C. to 50° C.

Figure 4A:
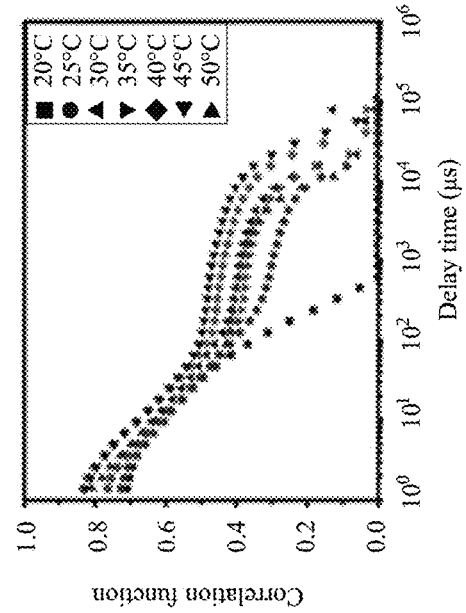
FIGS. 4A to 4D are dynamic light scattering (DLS) patterns of four ratios of the hydrogel compositions with thermos-sensitive and ionic reversible properties according to one embodiment of the present disclosure.
Figure 4B:
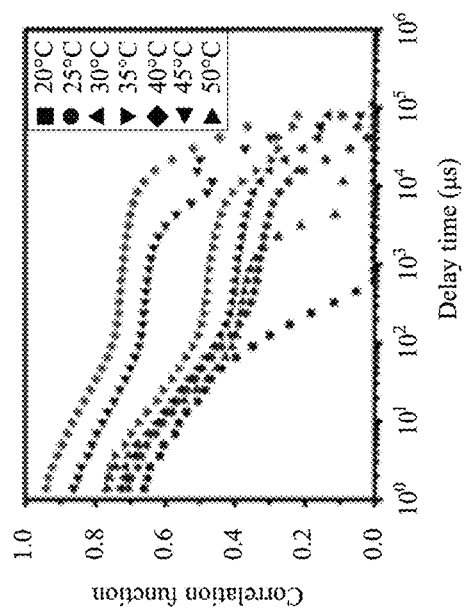
Figure 4C:
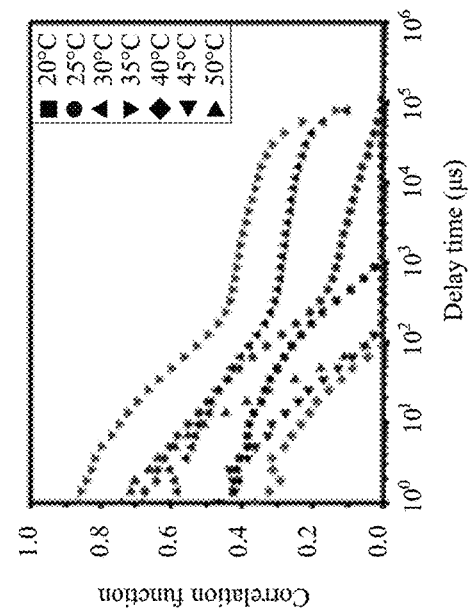
Figure 4D:
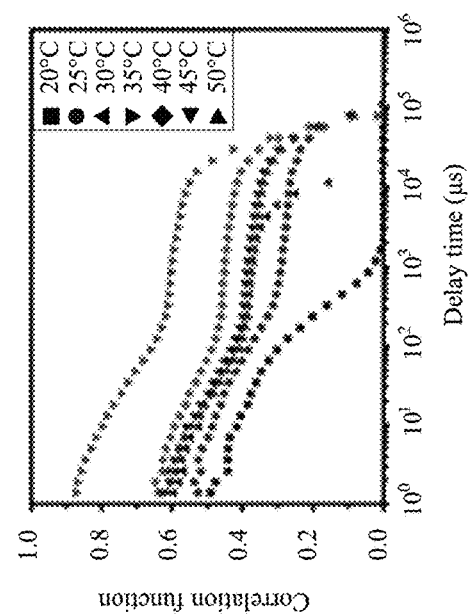

FIGS. 4A to 4D as shown herein are respectively four DLS patterns of 1.5 g Plu-150 mg Alg, 1.5 g Plu-100 mg Alg, 1.5 g Plu-50 mg Alg, and 1.5 g Plu-25 mg Alg of the hydrogel composition with thermos-sensitive and ionic reversible properties. Since 20° C. had exceeded the critical micelle concentration (CMC), the correlation function dropped significantly at the same delay time. As the temperature rose, polymer chains began to entangle and arranged to form a layered structure. Therefore, the movement of particles was restricted, causing the correlation function to rise. After exceeding 40° C., the decline of the correlation function gradually increased. The possible reason is that the hydrogel composition began to melt, so that the particles in the hydrogel composition started to move again, causing the correlation function to drop. FIG. 4A is the DLS image with the highest sodium alginate content. Because of the high content of the high sodium alginate, it may affect the gelation effect, so the aforementioned decline in the correlation function is less obvious.

Example 3. Sol-Gel Transition of the Hydrogel Composition with Thermos-Sensitive and Ionic Reversible Properties Four sodium alginate weights 150/100/50/25 mg with Plu solution having weight volume ratios from 12.5% to 27.5% (% w/v) were heated from 5° C. to 70° C., measured every 5° C., and maintained each temperature for 10 minutes. In order to confirm whether different ratios of the hydrogel compositions becomes a gel state (gel or colloid), the sample tubes containing the different ratios of the hydrogel compositions were turned upside down. If no liquid flows down after one minute, it can be confirmed that this concentration of the solution has a gel formation.

Figure 5:
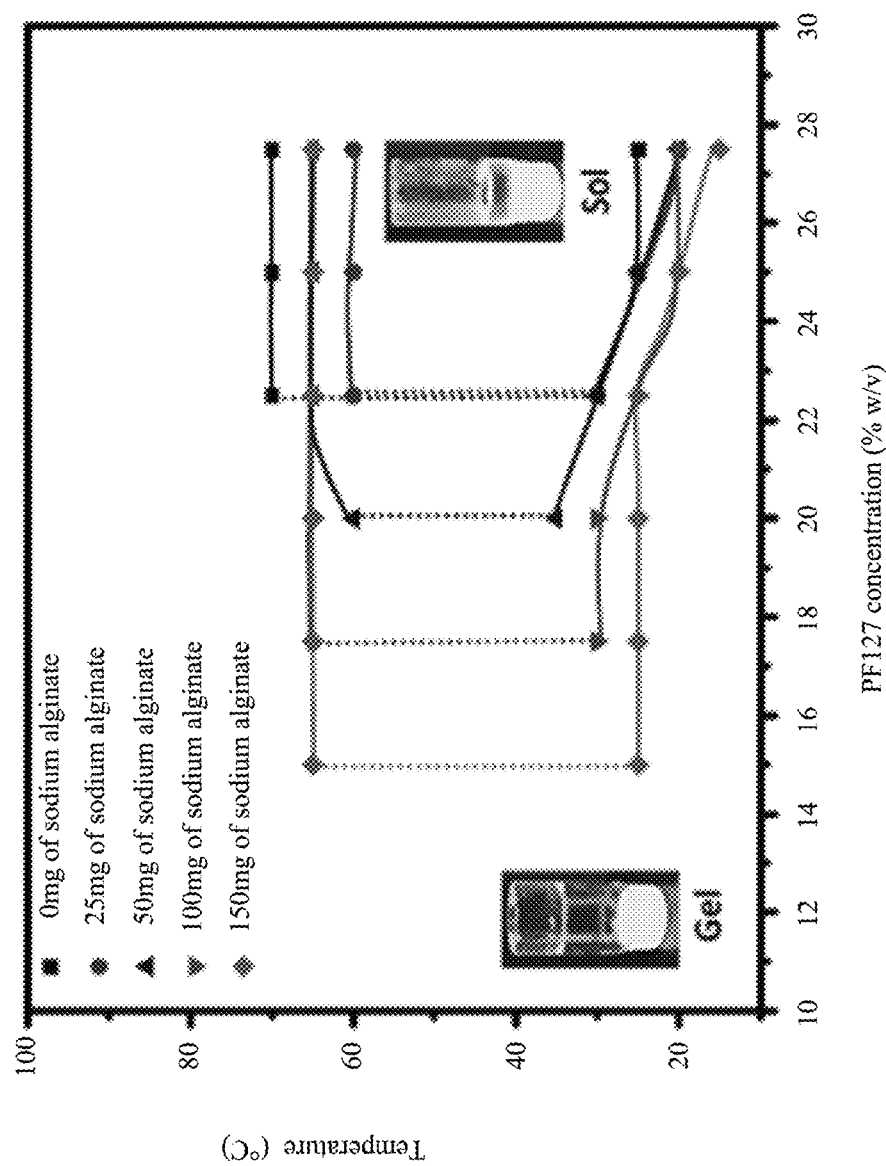
FIG. 5 is a solution state (Sol)-gel state (Gel) transition diagram of the hydrogel composition with thermos-sensitive and ionic reversible properties according to one embodiment of the present disclosure.

Referring to FIG. 5, the higher the concentration of sodium alginate, the lower the temperature and concentration of pluronic that can exhibit gelation, so that the reversibility (reverse to the solution state) was unobvious. The reason may be that the hydroxyl group of alginate can be firmly combined with the crosslinked pluronic, so alginate will affect the gel forming temperature and gel strength of pluronic. On the contrary, the lower the concentration of alginate, the higher the temperature and concentration of pluronic that can exhibit gelation, so that the reversibility was obvious.

Figure 6:
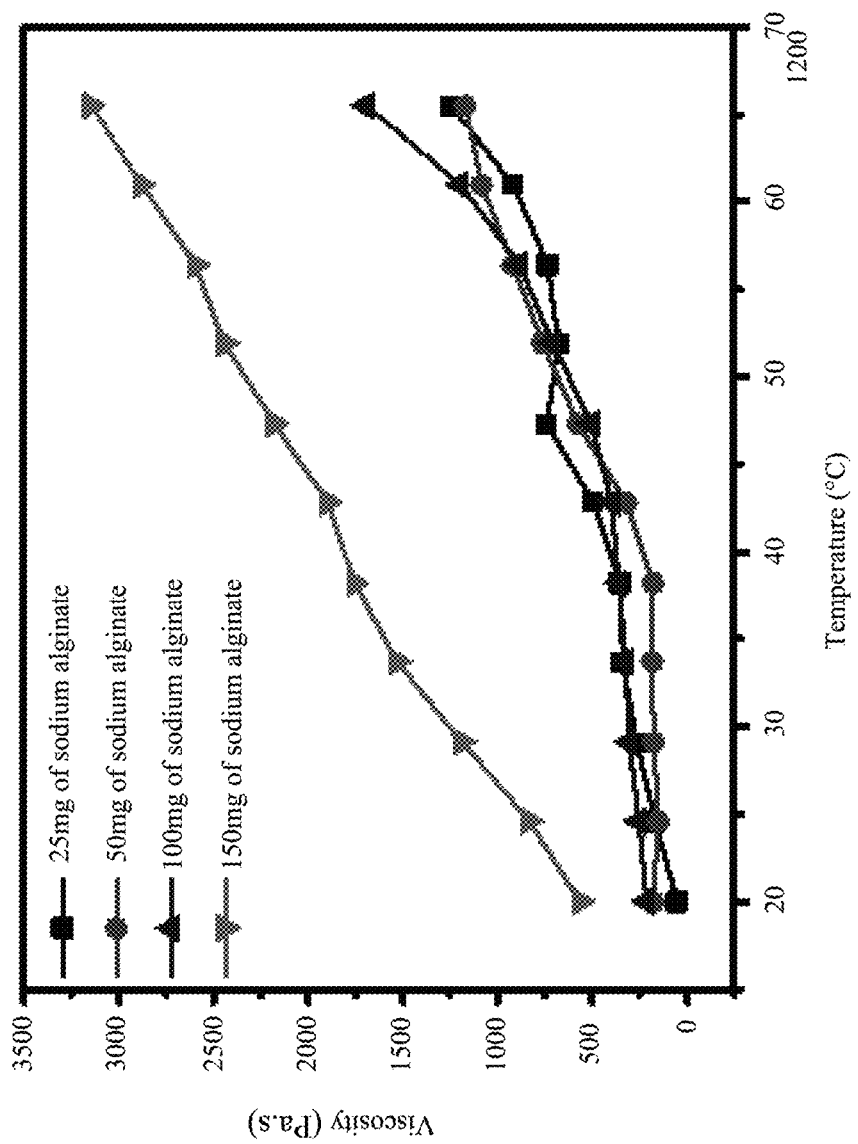
FIG. 6 is a line chart showing the change in viscosity of a fixed ratio of Plu with different ratios of sodium alginate including from 25 mg to 150 mg according to one embodiment of the present disclosure.

Example 4. The Gelation Point Analysis of the Hydrogel Composition with Thermos-Sensitive and Ionic Reversible Properties The hydrogel compositions with thermos-sensitive and ionic reversible properties were prepared by four weight ratios of Plu-Alg according to the Preparation 1. When the four hydrogel compositions were in the gel state, the viscosity change from high temperature to low temperature was measured. FIG. 6 indicates the viscosity of sodium alginate from 25 mg to 150 mg, wherein when the hydrogel compositions with thermos-sensitive and ionic reversible properties had 25 mg to 150 mg sodium alginate, the viscosities were similar and low. This indicates that reversibility is obvious and fluidity is great, the hydrogel composition can be used as a choice of thermally reversible wound dressings. When the content of sodium alginate is 150 mg, the reversibility is not obvious because of strong mechanical properties.

Figure 7:
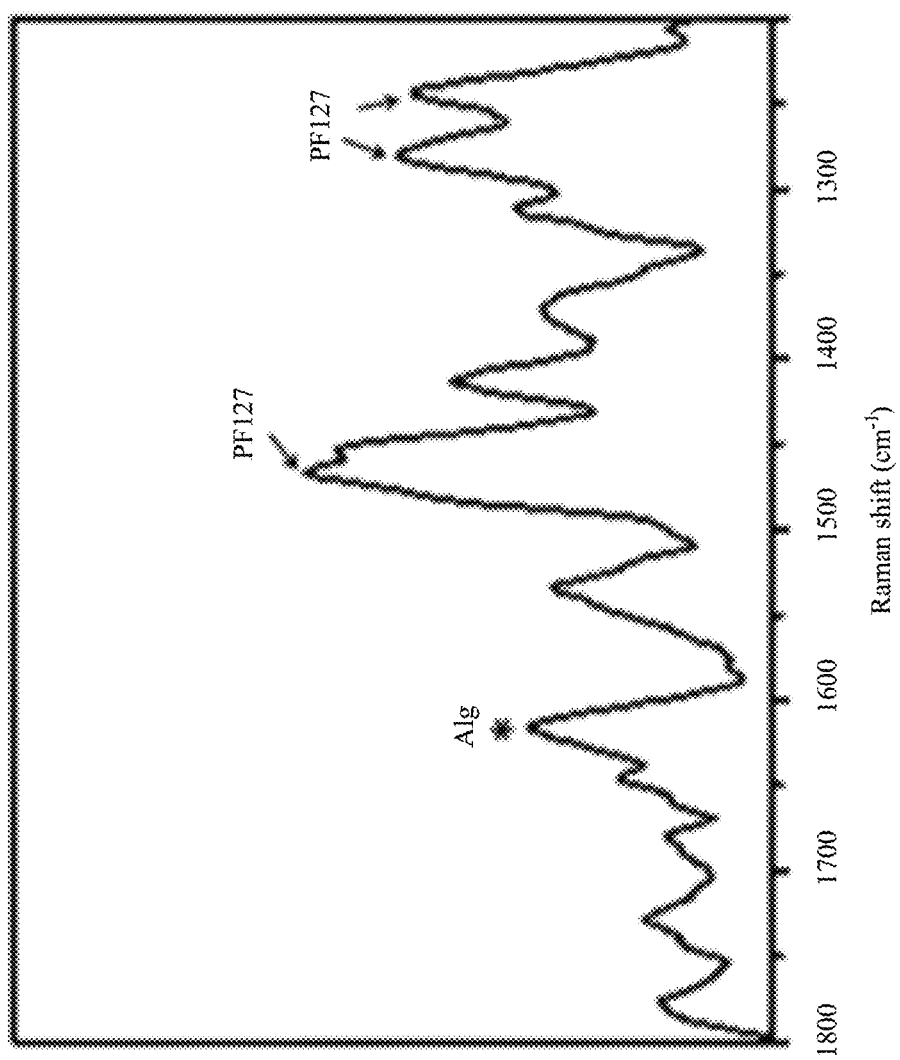
FIG. 7 shows the Raman spectrum of 1.5 g Plu-25 mg Alg hydrogel composition with thermos-sensitive and ionic reversible properties according to one embodiment of the present disclosure, in which "*" represents a characteristic peak of alginate (Alg), and "PF127" represents characteristic peaks of Pluronic® F127.
Figure 8A:
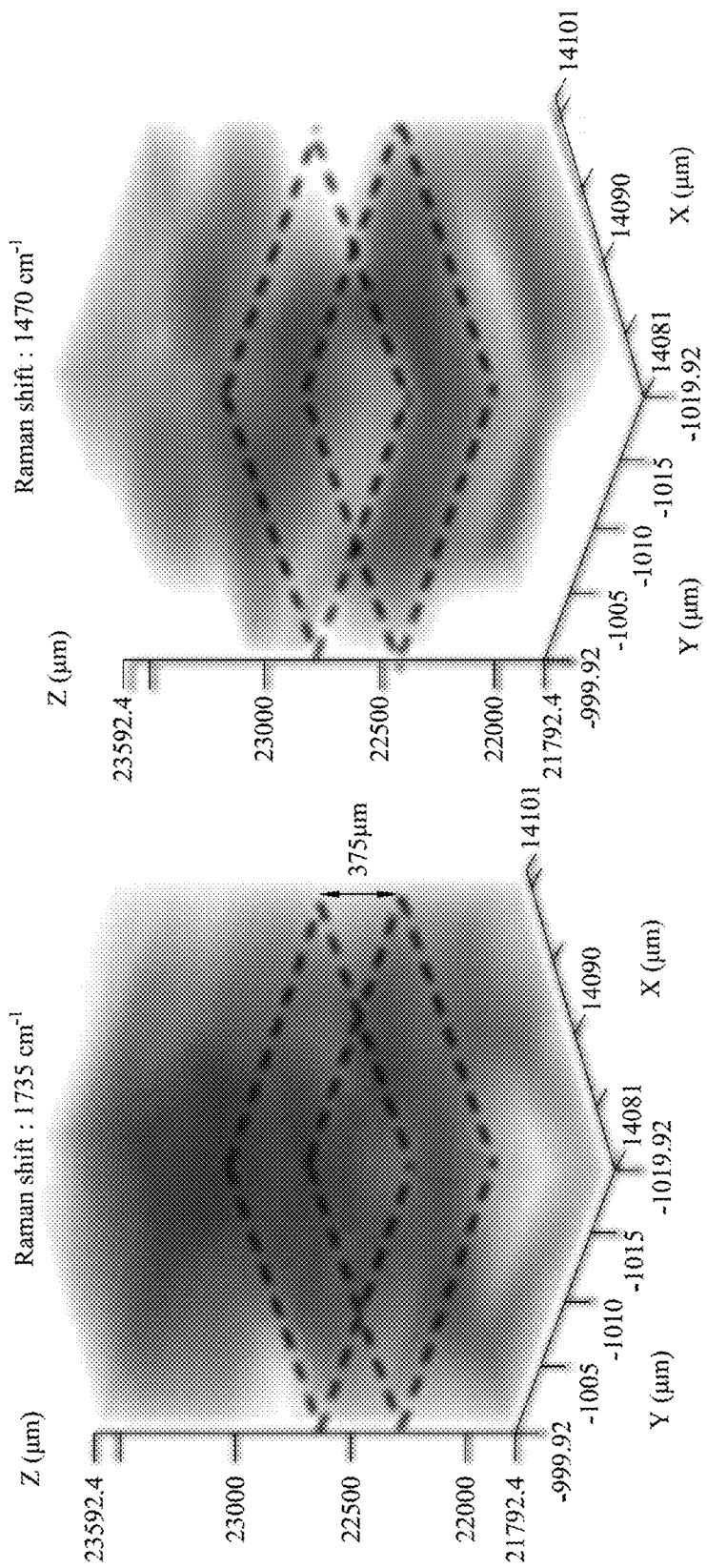
FIGS. 8A to 8D show 3D Raman microscopy images of the hydrogel compositions with thermos-sensitive and ionic reversible properties having different amounts of alginate according to one embodiment of the present disclosure. The Plu in each figure is 1.5 g, the left side of each figure is the analysis of the characteristic peak of alginate, and the right side of each figure is the analysis of the characteristic peak of polyoxyethylene (PEO).
Figure 8B:
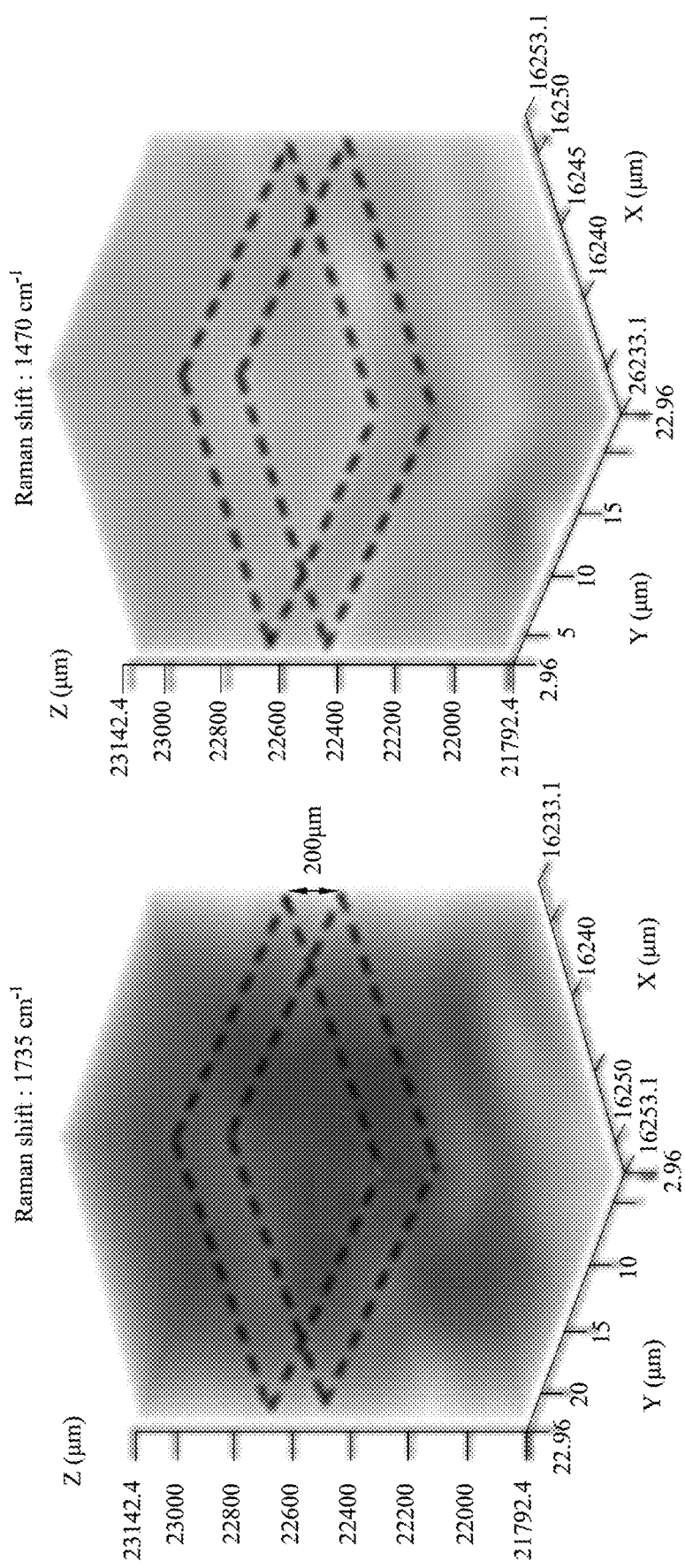
Figure 8C:
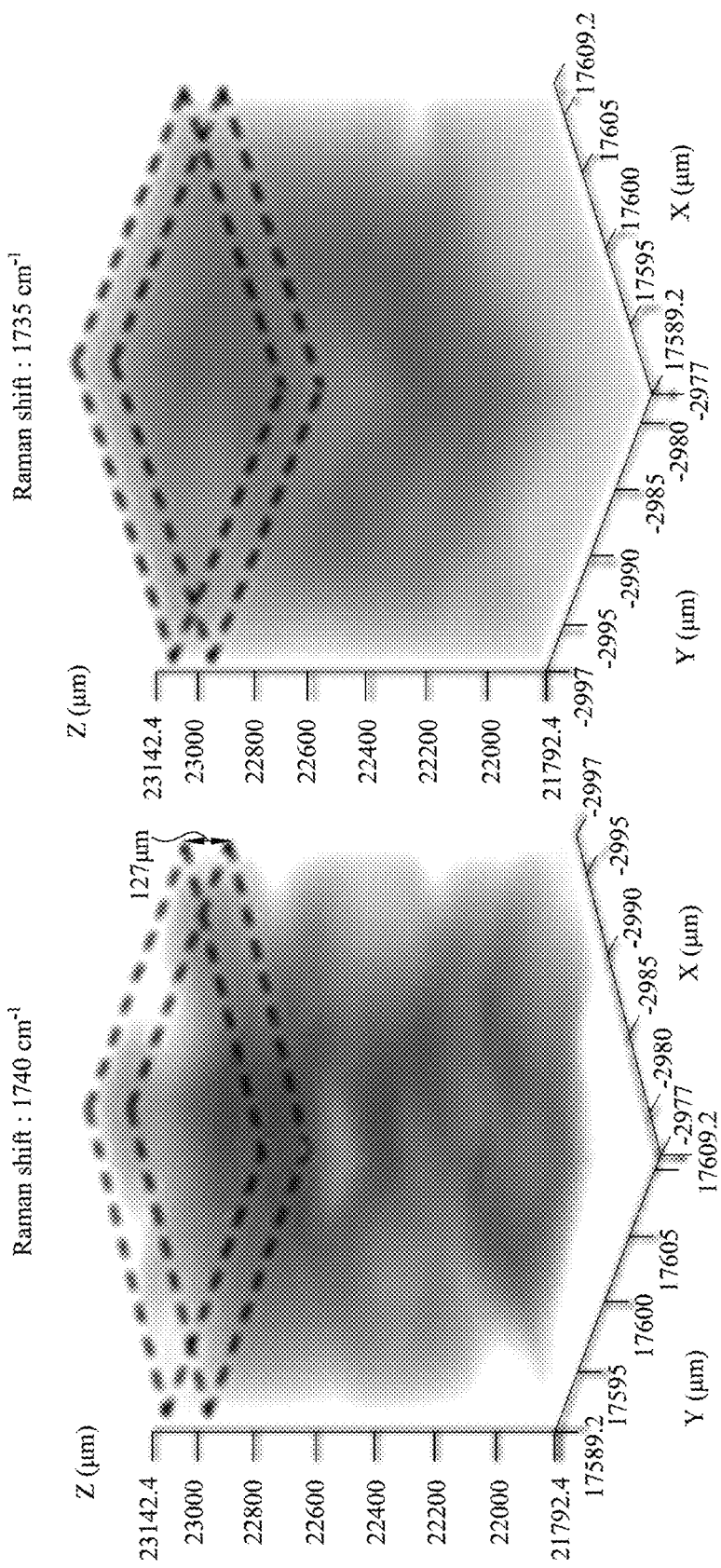
Figure 8D:
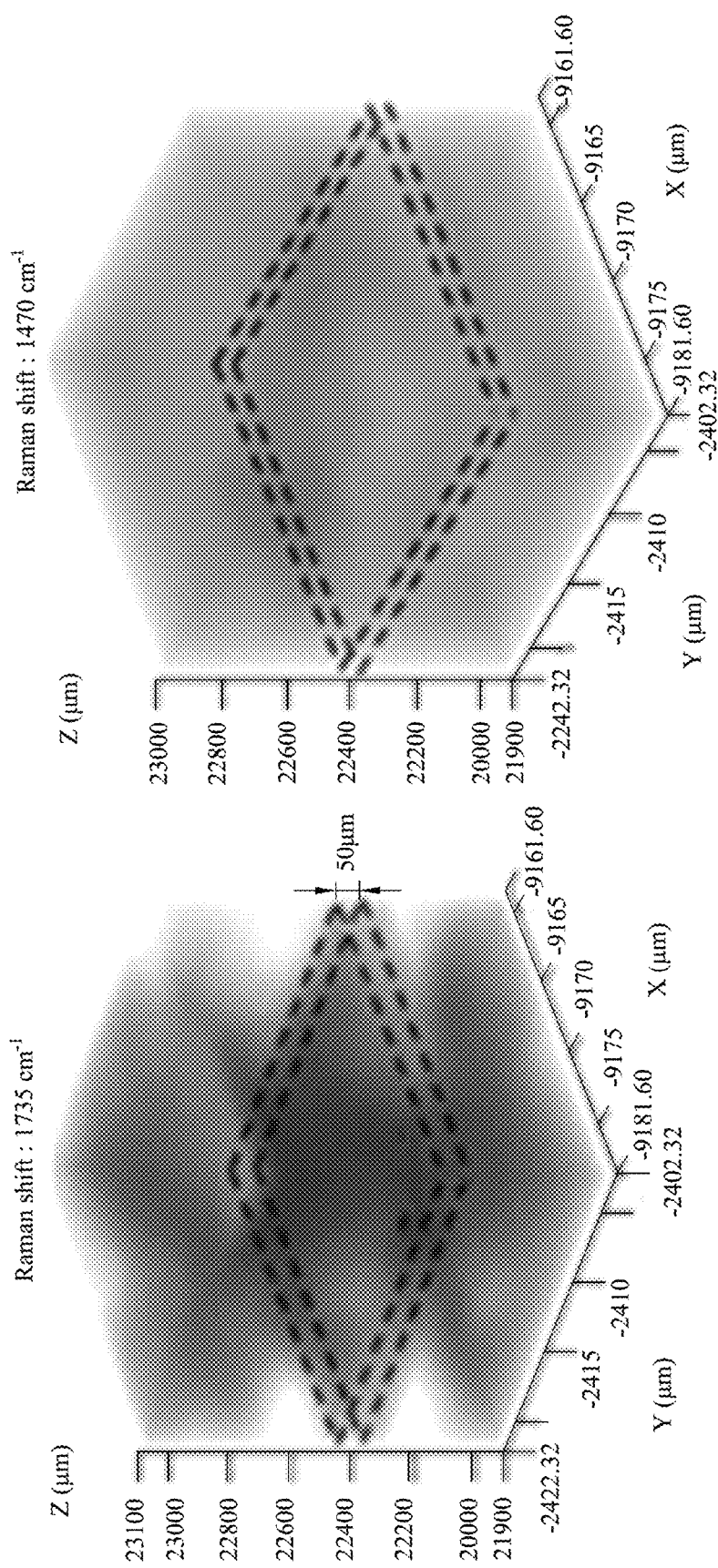

Example 5. Raman Spectroscopy Analysis of Hydrogel Composition with Thermos-Sensitive and Ionic Reversible Properties As shown in FIG. 7, FIG. 7 shows the Raman spectrum of 1.5 g Plu-25 mg Alg hydrogel composition with thermos-sensitive and ionic reversible properties. The content was calculated by the characteristic peaks of two different substances (pluronic and alginate) to obtain the element distribution image. The Raman shift peaks at about 1230 to 1250 $cm^{-1}$, about 1265 to 1285 $cm^{-1}$, and about 1460 to 1490 $cm^{-1}$ were characteristic peaks of polyoxyethylene (PEO) in pluronic, and the Raman shift peak at about 1605 to 1625 $cm^{-1}$ was the characteristic peak of alginate.

The 3D Raman microscopy image can scan multiple points on one surface in a space, and calculate the intensity of different material characteristic peaks at each point to further calculate the distribution characteristics of the material. The hydrogel compositions with thermos-sensitive and ionic reversible properties were prepared by four weight ratios of Plu-Alg according to the Preparation 1, and the characteristic peak value of PEO [1486.09[1469.09-1478.09]] and the characteristic peak value of alginate [1757.09[1751.09-1771.09]] were used for stereo microscopy. FIGS. 8A to 8D are 3D Raman microscopic images of the hydrogel composition with thermos-sensitive and ionic reversible properties containing 1.5 g Plu and different contents of alginate, wherein alginate is 150 mg in FIG. 8A, 100 mg in FIG. 8B, 50 mg in FIG. 8C, 25 mg in FIG. 8D. From the Raman mapping image, the hydrogel composition with thermos-sensitive and ionic reversible properties of the present disclosure had a layered structure, and the distance between layers varied from about 40 μm to about 600 μm, such as, 375 μm, 200 μm, 127 μm, and 90 μm in FIGS. 8A to 8D, respectively. The difference of the distance between layers could be related to the content of alginate, the more alginate content, the more the amount of alginate cross-linked between the pluronic layers to form the hydrogel composition, so that the distance between layers are larger.

Figure 9C:
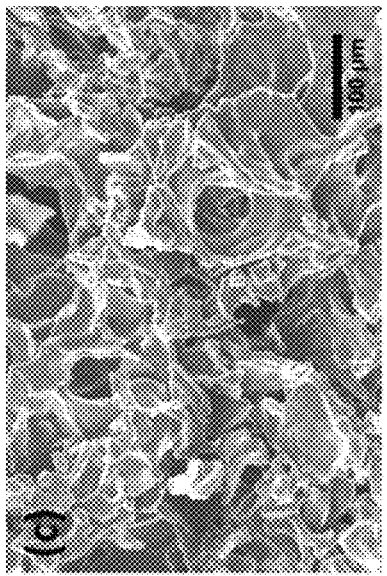
FIGS. 9A to 9F are scanning electron microscope (SEM) images showing the hydrogel compositions with thermos-sensitive and ionic reversible properties having different amounts of alginate according to one embodiment of the present disclosure.
Figure 9B:
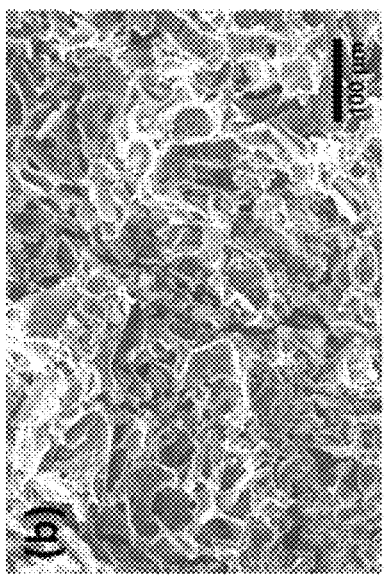
Figure 9A:
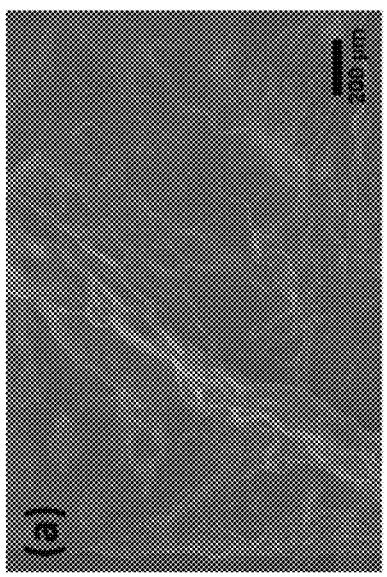
Figure 9F:
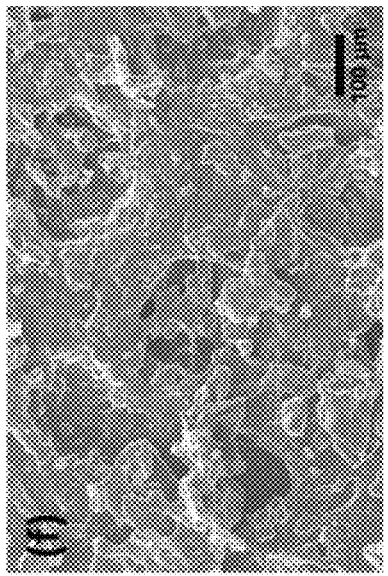
Figure 9E:
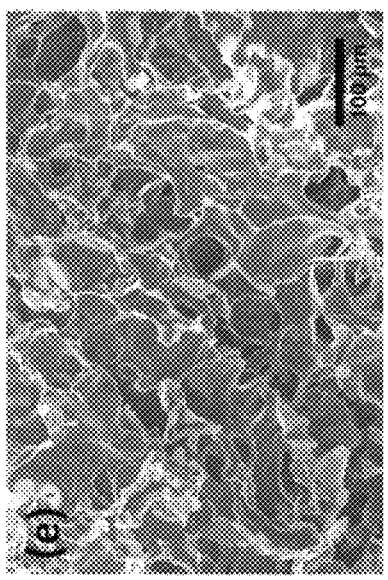
Figure 9D:
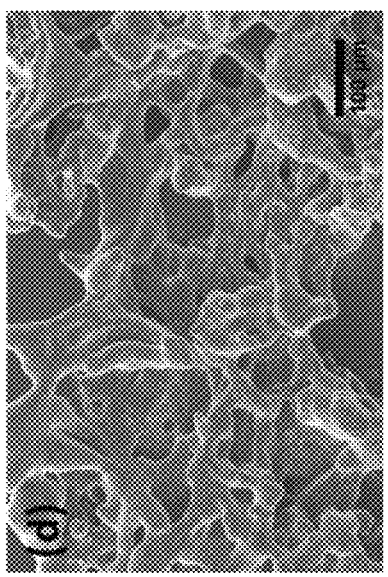

Example 6. Electron Microscopy of Hydrogel Composition with Thermos-Sensitive and Ionic Reversible Properties The sample was hit by the electron beam generated from the scanning electron microscope, and then a secondary electron imaging generated from the sample could observe the morphological characteristics of the surface of the sample. FIGS. 9A to 9F include scanning electron microscope (SEM) images showing the hydrogel compositions with thermos-sensitive and ionic reversible properties having different amounts of alginate, wherein FIG. 9A shows 150 mg of alginate crosslinked with calcium, FIG. 9B shows 15% (w/v) PF127, FIG. 9C shows 15% (w/v) PF127 mixed with 25 mg calcium alginate, FIG. 9D shows 15% (w/v) PF127 mixed with 50 mg calcium alginate, FIG. 9E shows 15% (w/v) PF127 mixed with 100 mg of calcium alginate, and FIG. 9F shows 15% (w/v) PF127 mixed with 150 mg of calcium alginate. The hydrogel composition with thermos-sensitive and ionic reversible properties prepared from the Preparation 1 generated network structure and formed a plurality of pores, and diameters of the pores were from 50 μm to 250 μm, especially the pores in the hydrogel composition containing 1.5 g Plu-25 mg Alg (FIG. 9C) were the most obvious. FIG. 9F shows the 1.5 g Plu-150 mg Alg hydrogel composition with fewer pores, and non-porous part was similar to the SEM image of pure alginate gel (FIG. 9A). As the proportion of alginate decreases, more and more pores were present and obvious, and the result was closer to the structure of pure pluronic gel (FIG. 9B).

Example 7. Cytotoxicity Test of the Hydrogel Composition with Thermos-Sensitive and Ionic Reversible Properties Test procedure of the hydrogel composition in solution state: 1.5 g Plu-25 mg Alg of the hydrogel composition with thermos-sensitive and ionic reversible properties prepared from the Preparation 1 was mixed with medium for 24 hours, and then centrifuged at 1,000 rpm for 5 minutes to obtain a supernatant as a first mixture. Next, the first mixture was added to human skin keratinocytes (HaCaT) and cultured for 24 hours for cell metabolic activity test (MTT assay), in order to evaluate the biocompatibility of the hydrogel composition. Test procedure of the hydrogel composition in gel state: 1.5 g Plu-25 mg Alg of the hydrogel composition prepared from the Preparation 1 was mixed with medium for 24 hours, and then removed the gel state hydrogel composition to obtain a second mixture. Next, the second mixture was added to human skin keratinocytes (HaCaT) and cultured for 24 hours for cell metabolic activity test (MTT assay), in order to evaluate the biocompatibility of the hydrogel composition. According to the guidelines for in vitro cytotoxicity determination of medical devices (ISO10993-5, Biological Evaluation of Medical Devices-Part 5: Tests for Cytotoxicity: In Vitro Methods, 1992), if the survival rate of cells exposed to the test substance exceeds 70%, the test substance is non-cytotoxic.

Figures 10A, 10B:
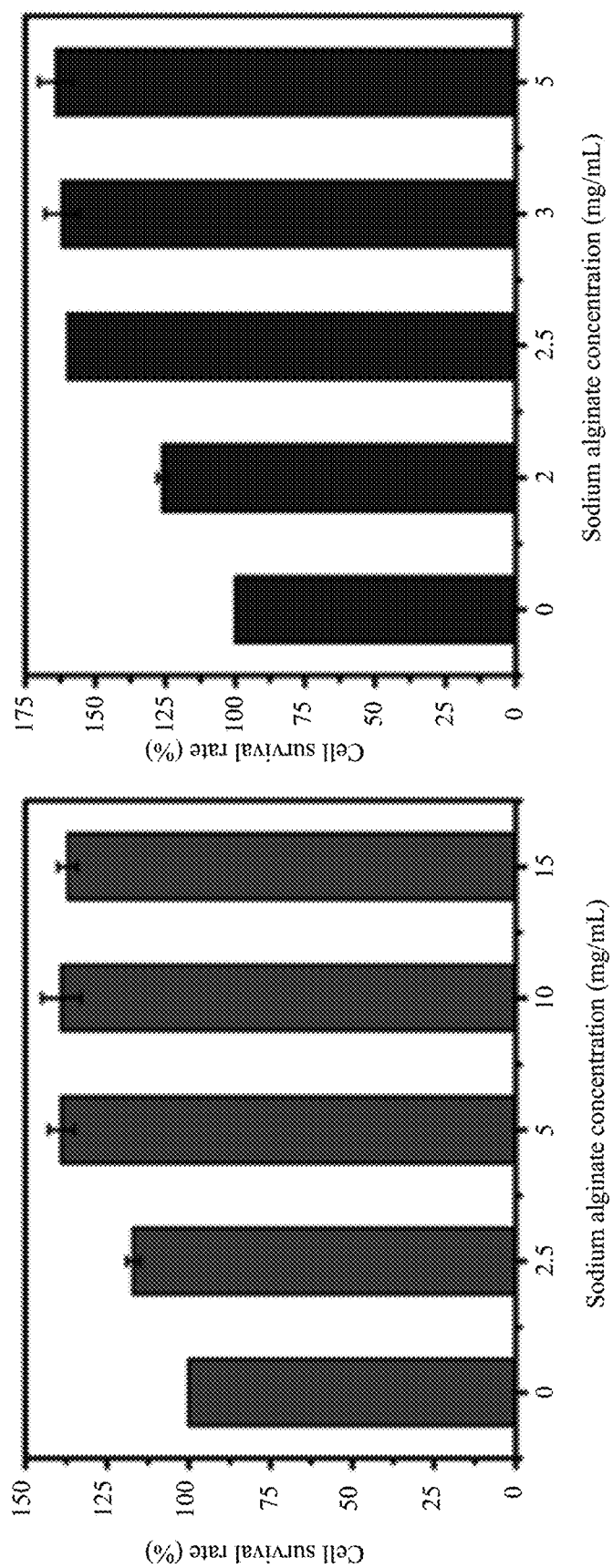

FIGS. 10A to 10B indicate bar graphs of the cytotoxicity test of the hydrogel compositions with thermos-sensitive and ionic reversible properties, in which FIG. 10A shows the cell survival rate of human skin keratinocytes (HaCaT) treated with the hydrogel composition in the solution state (before gelation, without calcium ions), and FIG. 10B shows the cell survival rate of human skin keratinocytes (HaCaT) treated with the hydrogel composition in the gel state (after gelation, with calcium ions). As shown in FIGS. 10A and 10B, whether the hydrogel composition is in gel state (FIG. 10B) or in solution state (FIG. 10A), the cell survival rate is greater than 100%, which means that the hydrogel composition with thermos-sensitive and ionic reversible properties of the present disclosure is not cytotoxic.

Example 8. Solubility Experiment of Hydrogel Microsphere

The hydrogel microsphere with thermos-sensitive and ionic reversible properties obtained from the Preparation 2 was performed the solubility experiment. Specifically, sodium alginate (hereinafter Alg) was dissolved in deionized water to become 2 wt % Alg solution. 2 wt % and 20 wt % of Pluronic® F-127 (hereinafter Plu) were respectively added in to two solutions of 2 wt % Alg and stirred at 4° C. until the powder was dissolved. Then, each of Alg/Plu solutions filled into syringe was respectively titrated into 20° C. and 40° C. calcium solutions at a rate of 0.1 mL/min to form microspheres with a particle size of about 2 mm. 20 microspheres were collected and stored at the temperature during titration for 1 hour.

50 mL 0.005M EDTA solutions were respectively prepared and heated to 20° C. and 40° C., the above microspheres were respectively added into the EDTA solutions, and the microspheres were taken out at 0, 10, 20, 30, 40, 50, and 60 minutes, the wiping paper absorbed the moisture on the surface of the microspheres and the microspheres were weighed.

Figures 11A, 11B:
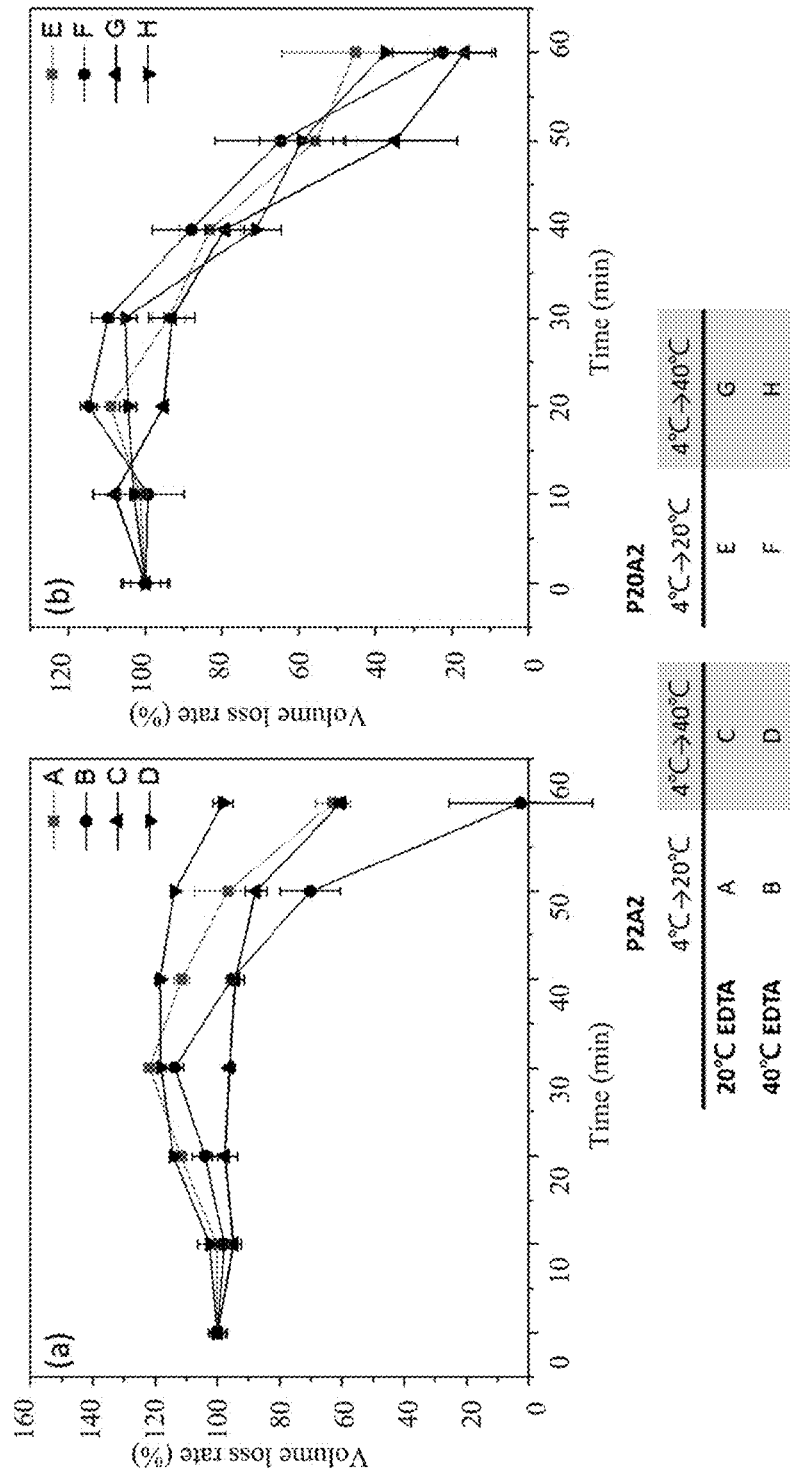
FIGS. 11A to 11B are line graphs showing weight changes of different mixing ratios of the hydrogel compositions with thermos-sensitive and ionic reversible properties under different titration temperatures and disintegration temperatures according to one embodiment of the present disclosure.

As shown in FIGS. 11A and 11B, sample A to H were divided to:

(1) Plu/Alg mix ratio of 2:2 (P2A2)
Sample A indicates that 4° C. Plu/Alg was added with Ca-EDTA to gel at 20° C., and then 20° C. EDTA was used to perform a disintegration test.
Sample B indicates that 4° C. Plu/Alg was added with Ca-EDTA to gel at 20° C., and then 40° C. EDTA was used to perform a disintegration test.
Sample C indicates that 4° C. Plu/Alg was added with Ca-EDTA to gel at 40° C., and then 20° C. EDTA was used to perform a disintegration test.
Sample D indicates that 4° C. Plu/Alg was added with Ca-EDTA to gel at 40° C., and then 40° C. EDTA was used to perform a disintegration test.
(2) Plu/Alg mix ratio of 20:2 (P20A2)
Sample E indicates that 4° C. Plu/Alg was added with Ca-EDTA to gel at 20° C., and then 20° C. EDTA was used to perform a disintegration test.
Sample F indicates that 4° C. Plu/Alg was added with Ca-EDTA to gel at 20° C., and then 40° C. EDTA was used to perform a disintegration test.
Sample G indicates that 4° C. Plu/Alg was added with Ca-EDTA to gel at 40° C., and then 20° C. EDTA was used to perform a disintegration test.
Sample H indicates that 4° C. Plu/Alg was added with Ca-EDTA to gel at 40° C., and then 40° C. EDTA was used to perform a disintegration test.

FIG. 11A is 2 wt % Plu-2 wt % Alg, FIG. 11B is 2 wt % Plu-20 wt % Alg, the weight changes of the two ratios at different titration temperature and disintegration temperature were recorded. As shown in FIG. 11A, under Plu/Alg ratio of 2:2, since the samples C and D were titrated to 40° C. calcium ion solutions had reached the Plu gelation temperature, the hydrogel microsphere had ordered structure during gelation, and the weight loss curve had a flatter curve. On the contrary, since the samples A and B were titrated to 20° C. calcium ion solutions had not reached the Plu gelation temperature, only Alg could maintain the stability of the structure, so that a steeper weight loss curve was observed when the microspheres were immersed in the EDTA solution. FIG. 11B is Plu/Alg ratio of 20:2, the correlation between titration temperature and disintegration rate could not be observed from the curve of weight change, because the large amount of Plu polymer segments in the hydrogel sample had affected the Alg gelation. Therefore, comparing the samples E, F, G, and H to samples C and D in FIG. 11A, although the Plu gelation temperature had reached, the ordered structure could not be formed, so that the slope of the weight loss curves of the samples E, F, G, and H were lower than that of samples C and D.

Example 9. Small-Angle X-Ray Scattering Pattern of the Hydrogel Microsphere

Figure 12D:
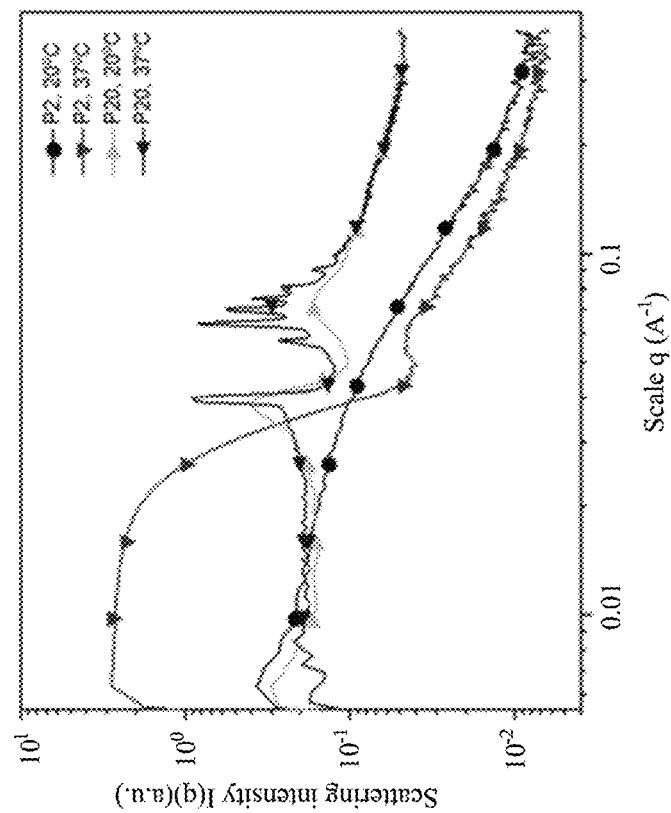
Figure 12C:
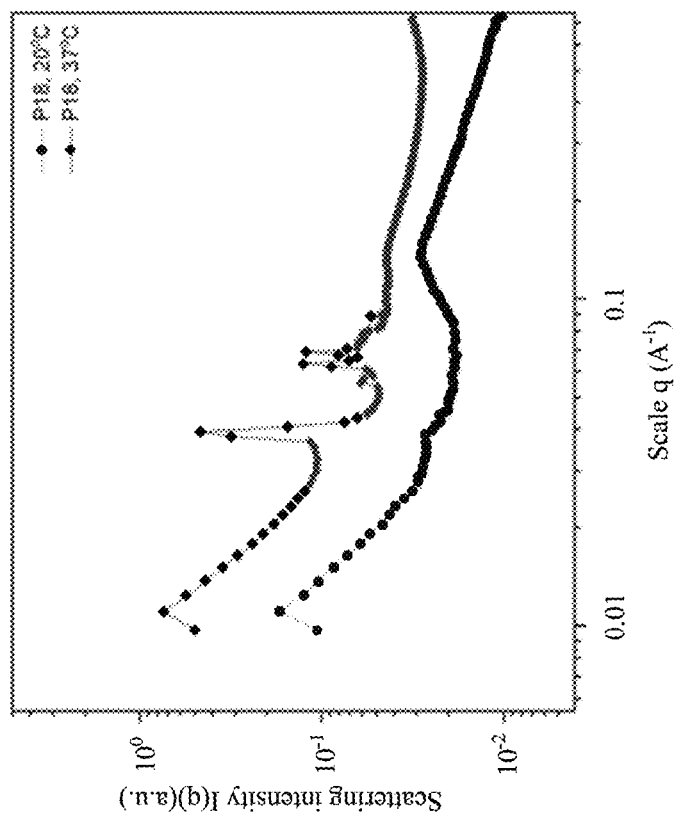

Small-angle X-ray scattering (SAXS) uses X-ray and electron scattered rays to perform non-destructive scanning of the hydrogel microsphere with thermos-sensitive and ionic reversible properties of the Preparation 2, and the distribution of material microstructure was qualitatively observe. FIG. 12A shows the hydrogel microspheres with the Plu/Alg mixing ratio of 2:2 (P2A2) and 18:2 (P18A2) gelling at 20° C. and 37° C., FIG. 12B is a partial enlarged view of FIG. 12A. FIG. 12C shows the Plu 18 wt % alone gelling at 20° C. and 37° C., FIG. 12D shows the changes in the scattering intensity of Plu 2 wt % (P2) and Plu 20 wt % (P20) gelling at 20° C. and 37° C.

As shown in FIGS. 12C to 12D, it can be observed that the hydrophilic and hydrophobic ends were aggregated at different concentrations of Plu because of the change of temperature. Micelles and gel form were respectively formed while critical micelle concentration (CMC)/critical micelle temperature (CMT) and critical gelation concentration (CGC)/LCST were reached. Obvious characteristic peaks appear between SAXS pattern from 0.03 $A^{-1}$ to 0.05 $A^{-1}$ and from 0.05 $A^{-1}$ to 0.1 $A^{-1}$ in the Plu 20 wt % sample. The signals appearing in these areas were the basis for determining the Plu phase transition. However, after Alg was added to Plu, Alg dominated the overall characteristic peak structure and partially suppressed the characteristics of Plu. This was verified by FIG. 12B, in the interval of 0.03 $A^{-1}$ to 0.1 $A^{-1}$, no obvious characteristic peak was observed in P2A2 no matter at 20° C. or 37° C., and the characteristic peak of Plu was disappeared when P18A2 at low temperature. However, the peak of scattering intensity could be observed in the interval of 0.05 $A^{-1}$ to 0.08 $A^{-1}$ after heating up (such as 37° C.). This means that the high-concentration sample (P18A2) should have a characteristic peak change when the gel was transformed into a micelle, and it is speculated that an ordered structure had occurred.

As above mentioned, the hydrogel compositions with thermos-sensitive and ionic reversible properties of the present disclosure are different from ordinary hydrogels on the market, and these hydrogel compositions are mostly transformed by environmental temperature, ion or acid-base changes. Cross-linking of the hydrogel compositions with thermos-sensitive and ionic reversible properties of the present disclosure is controlled through dual conditions—ions and temperature in the environment, the hydrogel compositions need giving ions and heating up at the same time to form a gel. Therefore, the characteristic is that changing a single condition cannot completely reverse from the gel state to the liquid state, the stability of the material structure in operation is easy to maintain, and this stable property can be used to develop some interesting applications as mentioned above.

In particular, the application of the hydrogel composition with thermos-sensitive and ionic reversible properties of the present disclosure includes: wound dressings, medical compositions, drug carriers, cell three-dimensional scaffolds, soluble microspheres and cell replenishment systems. As the wound dressings, the hydrogel composition with thermos-sensitive and ionic reversible properties of the present disclosure gel can be washed by ice saline to remove and replace. Therefore, it has the advantages of easy replacement, good in vitro and in vivo stability, high biocompatibility, and non-toxicity for use as a therapeutic aid.

When the hydrogel composition with thermos-sensitive and ionic reversible properties of the present disclosure is applied to the affected area or wound, the hydrogel composition is gelation by body temperature to keep the wound in a warm and humid environment. When the wound dressing needs to be changed and removed, it can be washed with ice water or PBS (which contains sodium can have the opportunity to replace calcium) to partially disintegrate the hydrogel composition with thermos-sensitive and ionic reversible properties having an ordered structure, thereby easily removing the wound dressing from the wound. In some embodiment, the hydrogel composition with thermos-sensitive and ionic reversible properties can be completely and quickly disintegrated with ice water containing ionic solution (such as 4° C. to 20° C. EDTA aqueous solution). Therefore, the hydrogel composition with thermos-sensitive and ionic reversible properties of the present disclosed will not stick to the affected area, and the composition can also avoid secondary damage to the affected area when removed.

In addition, the hydrogel composition with thermos-sensitive and ionic reversible properties of the present disclosed can be used as an injection-type local cancer treatment. The present disclosure discloses the concept of designing a composite hydrogel in vitro to improve the residence time and stability of pluronic. The present disclosure can effectively improve the temperature stability of pluronic by using calcium alginate or other polysaccharide polymers containing carboxylic acid groups. At the same time, the present disclosure also develops ion- and temperature-sensitive polymers that can be prepared into hydrogel or hydrogel microspheres. Furthermore, when the hydrogel composition with thermos-sensitive and ionic reversible properties of the present disclosure being as microspheres is soluble, therefore, after the cells are detached from the microspheres, the microspheres and the cultured cells can be separated.

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for preparing a hydrogel composition with thermos-sensitive and ionic reversible properties, comprising following steps:
   providing a thermos-sensitive polymer;
   providing an anionic polymer comprising polysaccharide having at least one carboxylic acid;
   dissolving and mixing the thermos-sensitive polymer and the anionic polymer in a solvent to obtain an initial solution; and
   performing a mixing process with the initial solution and an anionic crosslinking agent, wherein when the initial solution and the anionic crosslinking agent are in contact at a temperature over a lower critical solution temperature (LCST), crosslinking occurs to obtain the hydrogel composition with thermos-sensitive and ionic reversible properties, wherein the hydrogel composition with thermos-sensitive and ionic reversible properties has ordered structure in a gel state, and the hydrogel composition with thermos-sensitive and ionic reversible properties can reversibly transfer from the gel state to a solution state, wherein a weight ratio of the thermos-sensitive polymer and the anionic polymer is 1:0.02-0.12, wherein when the hydrogel composition contacts a metal chelate aqueous solution having a temperature lower than the LCST of the hydrogel composition, the hydrogel composition transfers from a gel state to a solution state.

2. The method of claim 1, wherein the thermos-sensitive polymer comprises amphiphilic triblock copolymer or N-isopropylacrylamide (NIPAAm).

3. The method of claim 2, wherein the amphiphilic triblock copolymer comprises poloxamer, the poloxamer is sequentially composed with poly-ethylene oxide (PEO)-poly-propylene oxide (PPO)-PEO, wherein the polysaccharide having the at least one carboxylic acid comprises mannuronic acid and guluronic acid.

4. The method of claim 3, wherein the polysaccharide is alginate.

5. The method of claim 1, wherein the step of dissolving and mixing the thermos-sensitive polymer and the ionic polymer in a solvent comprises a weight ratio of the thermos-sensitive polymer and the ionic polymer is from 1:0.001 to 1:0.6.

6. The method of claim 1, wherein the anionic crosslinking agent comprises one or more solutions of monovalent to tetravalent metal cations, or one or more solutions of monovalent to tetravalent metal cations and a metal chelating agent.

7. The method of claim 6, wherein the one or more solutions of monovalent to tetravalent metal cations are $Li^+$, $Na^+$, $K^+$, $Cu^+$, $Ag^+$, $Au^+$, $Cu^{+2}$, $Be^{+2}$, $Mg^{+2}$, $Ca^{+2}$, $Sr^{+2}$, $Ba^{+2}$, $Zn^{+2}$, $Sn^{+2}$, $Fe^{+2}$, $Pb^{+2}$, $Co^{+2}$, $Ni^{+2}$, $Mn^{+2}$, $Cd^{+2}$, $Au^{+3}$, $Al^{+3}$, $Ga^{+3}$, $In^{+3}$, $Fe^{+3}$, $Co^{+3}$, $Ni^{+3}$, $Ce^{+3}$, $Se^{+3}$, $Ce^{+4}$, $Se^{+4}$, $Ti^{+4}$, or a combination thereof.

8. The method of claim 1, wherein the step of dissolving and mixing the thermos-sensitive polymer and the ionic polymer in a solvent comprises obtaining the initial solution at a low temperature.

9. The method of claim 8, wherein the low temperature is from 0° C. to 20° C.

10. The method of claim 1, wherein the mixing process comprises dialysis, microfluidics, titration, electrospinning, emulsion polymerization, reprecipitation, or a combination thereof.

11. The method of claim 1, wherein the ordered structure comprises a face-centered cubic crystal structure, a body-centered cubic crystal structure, a hexagonal close-packed crystal structure, a layered structure, or a combination thereof.

12. A hydrogel composition with thermos-sensitive and ionic reversible properties, comprising:

a thermos-sensitive polymer; and an anionic polymer comprising polysaccharide having at least one carboxylic acid, wherein the thermos-sensitive polymer and the anionic polymer are mixed at a temperature over a lower critical solution temperature (LCST);

wherein the hydrogel composition is analyzed by Raman spectroscopy when the hydrogel composition is in a gel state, a Raman mapping image of the hydrogel composition presents an ordered structure, and the hydrogel composition can reversibly transfers from the gel state to a solution state;

wherein the hydrogel composition is analyzed by small-angle X-ray scattering (SAXS) when the hydrogel composition is in the gel state, the hydrogel composition comprises a scattering intensity peak, wherein a weight ratio of the thermos-sensitive polymer and the anionic polymer is 1:0.02-0.12, wherein when the hydrogel composition contacts a metal chelate aqueous solution having a temperature lower than the LCST of the hydrogel composition, the hydrogel composition transfers from a gel state to a solution state.

13. The hydrogel composition of claim 12, wherein the thermos-sensitive polymer comprises amphiphilic triblock copolymer or N-isopropylacrylamide (NIPAAm), and the ionic polymer comprises polysaccharide having at least one carboxylic acid.

14. The hydrogel composition of claim 13, wherein the amphiphilic triblock copolymer comprises poloxamer, the poloxamer is sequentially composed with poly-ethylene oxide (PEO)-poly-propylene oxide (PPO)-PEO, wherein the polysaccharide having the at least one carboxylic acid comprises mannuronic acid and guluronic acid.

15. The hydrogel composition of claim 14, wherein the polysaccharide is alginate.

16. The hydrogel composition of claim 14, wherein the ordered structure is a layered structure, the layered structure is composed of a plurality of layers, an interval between two adjacent layers of the plurality of layers is from about 40 μm to about 600 μm.

17. A carrier comprising the hydrogel composition with thermos-sensitive and ionic reversible properties according to claim 12, wherein a form of the carrier comprises a wound dressing, a medical composition, a drug carrier, a cell three-dimensional scaffold or a soluble microsphere.

18. The method of claim 1, wherein the thermos-sensitive polymer is poloxamer, and the anionic polymer is alginate.

19. The hydrogel composition of claim 12, wherein the thermos-sensitive polymer is poloxamer, and the anionic polymer is alginate.

* * * * *